US011935638B2

(12) United States Patent
Nguyen

(10) Patent No.: US 11,935,638 B2
(45) Date of Patent: Mar. 19, 2024

(54) SYSTEMS, APPARATUSES AND METHODS FOR MEDICAL DEVICE COMMUNICATION WITH ONE OR MORE REMOTE DEVICES

(71) Applicant: Becton, Dickinson and Company, Franklin Lakes, NJ (US)

(72) Inventor: Tony Hai Nguyen, Hopkinton, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 321 days.

(21) Appl. No.: 17/415,255

(22) PCT Filed: Dec. 20, 2019

(86) PCT No.: PCT/US2019/067865
§ 371 (c)(1),
(2) Date: Jun. 17, 2021

(87) PCT Pub. No.: WO2020/142270
PCT Pub. Date: Jul. 9, 2020

(65) Prior Publication Data
US 2022/0059205 A1  Feb. 24, 2022

Related U.S. Application Data

(60) Provisional application No. 62/786,746, filed on Dec. 31, 2018.

(51) Int. Cl.
*G16H 20/17* (2018.01)
*A61M 5/172* (2006.01)
*G16H 40/67* (2018.01)

(52) U.S. Cl.
CPC .......... *G16H 20/17* (2018.01); *A61M 5/1723* (2013.01); *G16H 40/67* (2018.01);
(Continued)

(58) Field of Classification Search
CPC ........ G16H 20/17; G16H 40/67; G16H 20/30; A61M 5/1723; A61M 2205/3553;
(Continued)

(56) References Cited

U.S. PATENT DOCUMENTS 9,215,075 B1  12/2015  Poltorak
2008/0303638 A1*  12/2008  Nguyen ................. G06Q 10/00
                                                    707/E17.014
(Continued)

FOREIGN PATENT DOCUMENTS

JP  2015-514449 A   5/2015
JP  20160097055 A   5/2016
(Continued)

OTHER PUBLICATIONS

International Search Report dated Apr. 28, 2020, which issued in counterpart PCT Patent Application No. PCT/US2019/67865.
(Continued)

*Primary Examiner* — Omar Casillashernandez
(74) *Attorney, Agent, or Firm* — Dickinson Wright PLLC

(57) ABSTRACT

Devices, systems and methods are provided to securely and wirelessly connect a medical device to a controller or smartphone with medical device control app, and to wirelessly connect the controller or smartphone with medical device control app to other devices providing additional integrated disease management (IDM) functions. At least two different wireless communication protocols are used depending on level of security needed, with greater security needed for exchange of medical device control operation commands and related data between the medical device and its controller or smartphone with medical device control app to avoid nefarious or unintended changes in medical device control. Exchanges of historical data or notifications relating to the medical device and requiring less security can be (Continued)

transmitted to the controller and/or the smartphone or other IDM devices using a different and more commonly used wireless communication protocol that may afford less security.

20 Claims, 23 Drawing Sheets

(52) U.S. Cl.
CPC ............... *A61M 2205/3553* (2013.01); *A61M 2205/3561* (2013.01); *A61M 2205/3592* (2013.01); *A61M 2205/502* (2013.01); *A61M 2205/52* (2013.01); *A61M 2230/201* (2013.01); *A61M 2230/63* (2013.01)

(58) Field of Classification Search
CPC ............. A61M 2205/3561; A61M 2205/3592; A61M 2205/502; A61M 2205/52; A61M 2230/201; A61M 2230/63; Y02D 30/70; H04B 1/18; H04B 1/3888; H04B 1/3827; H04B 1/385; H04B 1/40; H04L 69/18; H04M 1/72412; H04W 12/033; H04W 12/50; H04W 52/0258; H04W 4/38; H04W 4/80; H04W 52/0209; H04W 88/02
USPC .................................................... 340/539.12
See application file for complete search history.

(56) References Cited

U.S. PATENT DOCUMENTS

| | | |
|---|---|---|
| 2011/0021143 A1 | 1/2011 | Kapur et al. |
| 2013/0117696 A1* | 5/2013 | Robertson .............. G16H 20/10 715/763 |
| 2014/0203950 A1* | 7/2014 | Zdeblick ................ G16H 40/67 340/870.07 |
| 2015/0025503 A1* | 1/2015 | Searle .................... G16H 20/13 604/67 |
| 2015/0136158 A1* | 5/2015 | Stevens .................. A24F 40/53 131/329 |
| 2017/0281864 A1* | 10/2017 | Searle .................... G16H 40/63 |
| 2017/0312530 A1 | 11/2017 | Schilling et al. |
| 2018/0036469 A1* | 2/2018 | Crnkovich ............. G16H 20/17 |
| 2018/0103499 A1 | 4/2018 | Lee et al. |
| 2018/0242876 A1 | 8/2018 | Hughes et al. |
| 2023/0148909 A1* | 5/2023 | Bijan .................... A61B 5/1116 600/595 |

FOREIGN PATENT DOCUMENTS

| | | |
|---|---|---|
| JP | 2017-528212 A | 9/2017 |
| JP | 2017202795 A | 11/2017 |

OTHER PUBLICATIONS

Kevin Townsend et al: "Getting Started with Bluetooth Low Energy" In: "Getting Started with Bluetooth Low Energy", May 12, 2014 (May 12, 2014), O'Reilly Media, Inc., XP055206773.

* cited by examiner

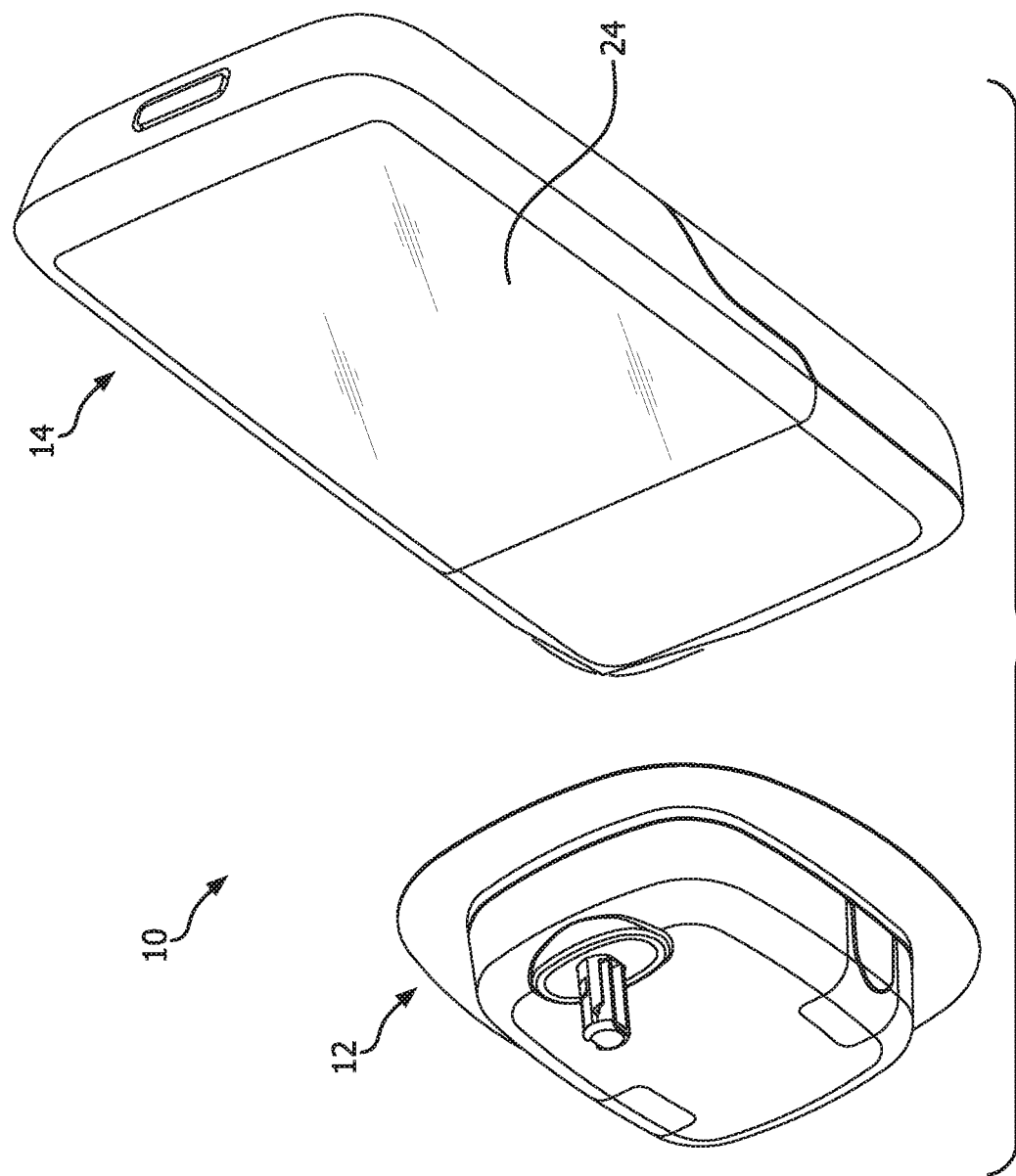

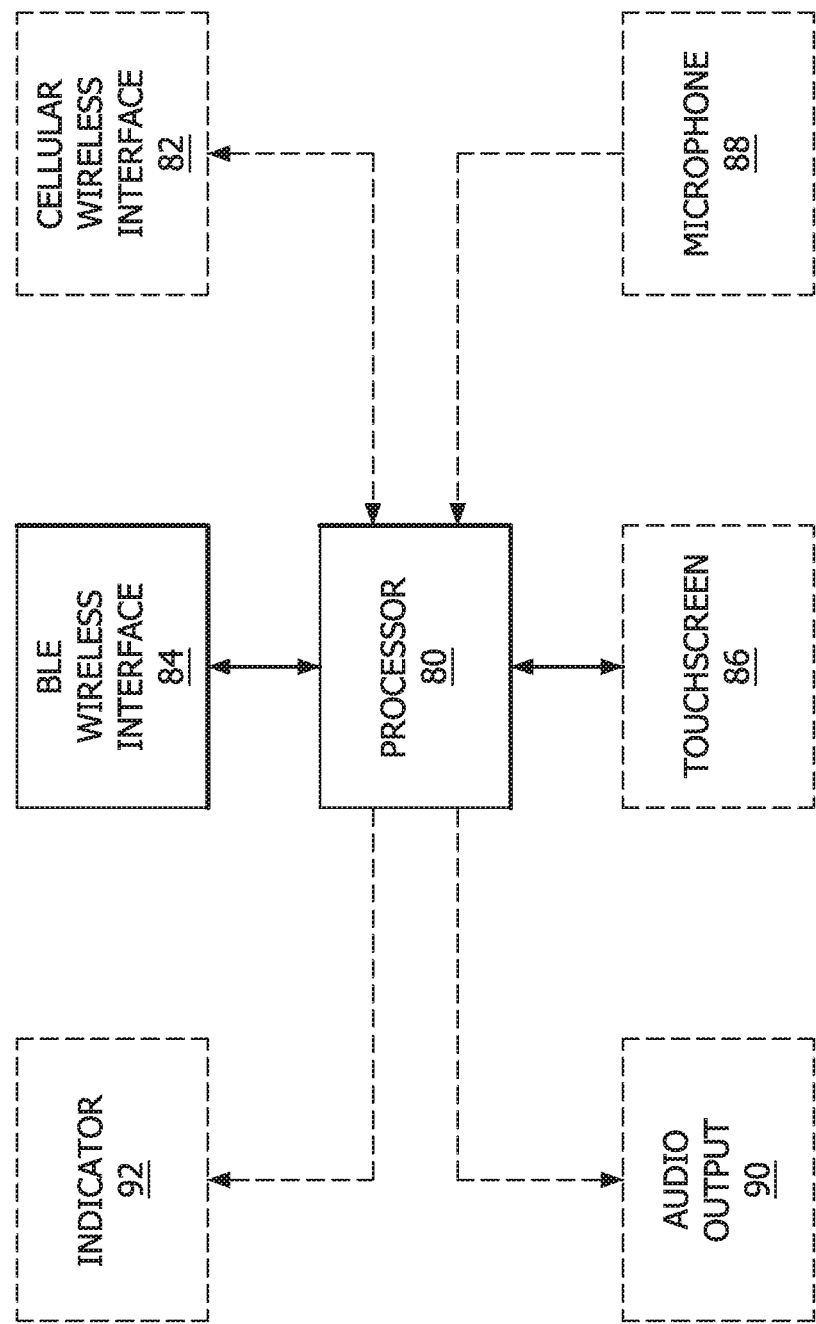

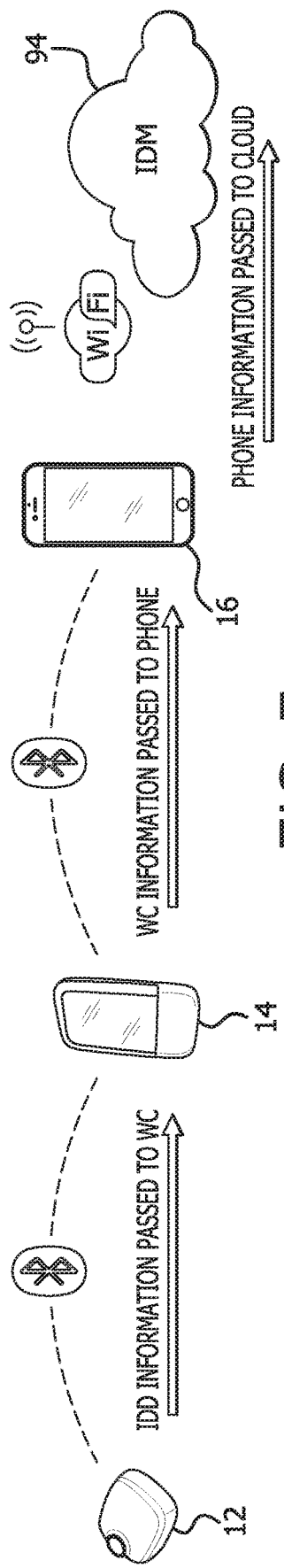
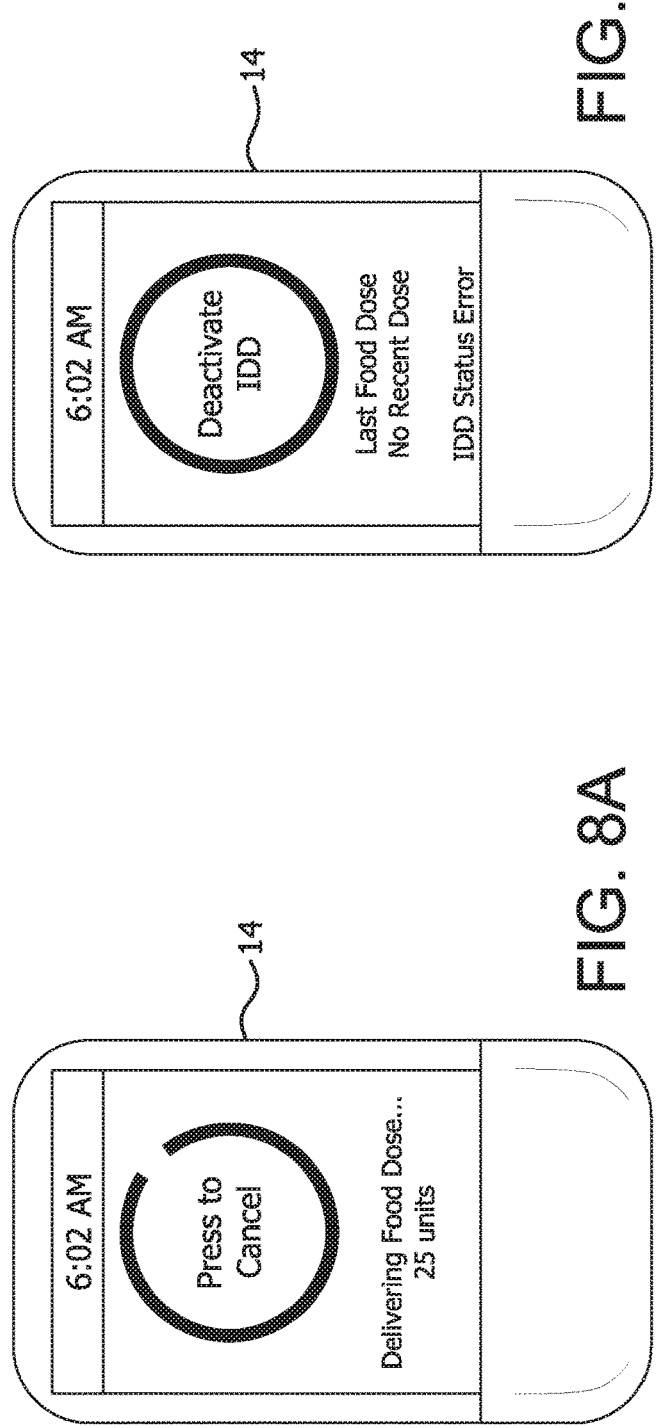
FIG. 7
FIG. 8A
FIG. 8B

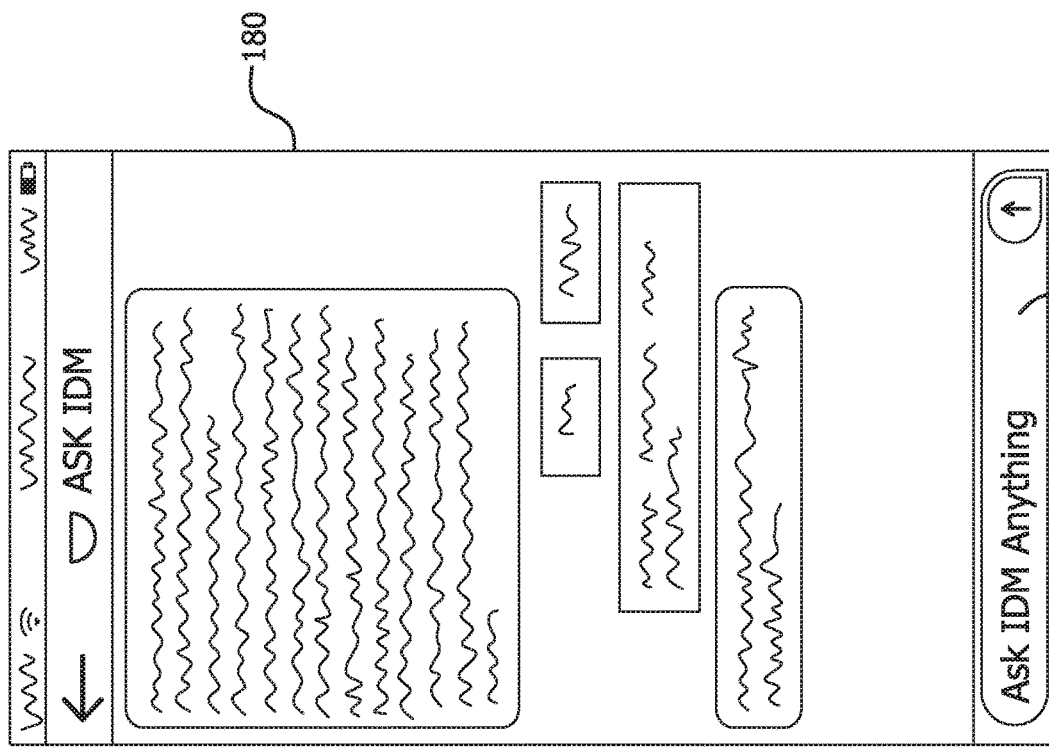

SYSTEMS, APPARATUSES AND METHODS FOR MEDICAL DEVICE COMMUNICATION WITH ONE OR MORE REMOTE DEVICES

BACKGROUND

Technical Field

Example embodiments herein relate to systems, methods and apparatuses for communications between wearable or portable medical devices and other devices, and for enhanced security of communications of medical device control signals from remote devices.

Description of Related Art

Demand for on-body or wearable medical devices and for body area network (BAN) medical devices (e.g., wireless controllers for on-body devices, and smartphones or smart watches with a medical condition management app and/or a health/fitness app) has been increasing, along with an increase in patients' and healthcare providers' desire for better and more convenient patient management of medical conditions such as diabetes. For example, one type of wearable medical device is a wearable medication delivery device that is worn against a patient's skin (e.g., a patch pump with cannula or needle inserted into the patient's skin), or a pump device that can be connected to a patient's belt, for example, and having an infusion set with tubing extending from the pump to an adhesive mount with a subcutaneous cannula.

A wearable medical device can communicate wirelessly with a separate dedicated controller or smartphone (e.g., a smartphone with app configured to wirelessly interface with the wearable medical device for various operations). Bluetooth® Low Energy (BLE), marketed as Bluetooth® Smart, is a wireless technology that provides an effective, low power protocol for wirelessly connecting devices, including devices that run on power sources such as coin cell batteries as can often be the case with wearable medical devices.

A concern with wirelessly controlling a wearable medical device, particularly a device that delivers medication to a patient's body, is security of the wireless control communication link against man-in-the-middle (MITM) and eavesdropping attacks. Of particular concern is security of a wearable medical device against nefarious attacks or unintentional attacks wherein control of the medical device is undesirably altered by another device. Another concern exists regarding protecting privacy of certain types of patient information stored in a wearable medical device and shared with other devices in a body area network, in a local area network (LAN), a wide area network (WAN) and/or the internet.

SUMMARY OF THE INVENTION

The problems are overcome, and additional advantages are realized, by illustrative embodiments described below.

It is an aspect of illustrative embodiments to provide a device for controlling a medical device, comprising: a radio frequency (RF) circuit configured to exchange RF signals with the medical device; a memory device; and a processing device connected to the RF circuit and the memory device and configured to employ a selected one of at least two wireless communication protocols to exchange, via the RF circuit, RF signals with the medical device, wherein the at least two wireless communication protocols comprises a first communication protocol that is employed by the processing device to pair the device with the medical device to securely send secure information chosen from configuration data, medical device operation data, and control signals to operate the medical device, and a second communication protocol that is employed by the processing device to pair with one or more devices different from the medical device an to send information chosen from medical device data and notifications that requires less security than the secure information to the one or more other devices.

In accordance with aspects of illustrative embodiments, the device is selected from the group of a handheld, dedicated controller for the medical device, and a smartphone having a medical device control app stored thereon for execution to control the medical device.

In accordance with aspects of illustrative embodiments, the first communication protocol limits pairing of the medical device to only the device for controlling operations of the medical device. For example, the first communication protocol is a Bluetooth® Low Energy (BLE) communication protocol. Further, the BLE communication protocol has no broadcast mode.

In accordance with aspects of illustrative embodiments, the first communication protocol is specific to the medical device and not usable by the one or more other devices to pair with the device.

In accordance with aspects of illustrative embodiments, the second communication protocol is a standard Bluetooth® protocol that is employed by the device to pair with the one or more other devices and comprises a broadcast mode to discover the one or more other devices.

In accordance with aspects of illustrative embodiments, the device is configured to operate as a hub in an integrated disease management (IDM) system by employing the first communication protocol to pair and exchange signals with the medical device, and the second communication protocol to pair and exchange signals with the one or more other devices, wherein the medical device is a medication delivery device and the one or more other devices are selected from the group consisting of a blood glucose monitor, a carbohydrate tracking device, and a physical exercise tracking device.

In accordance with aspects of illustrative embodiments, the device further comprises a portal app for passing through data relating to the medical device to another device, the portal app being configured to receive data transmitted from the medical device and provide it to another device and not store the data at the device.

In accordance with aspects of illustrative embodiments, the processing device is configured to determine which of the first communication protocol and the second communication protocol to employ to transmit signals via the RF circuit depending on a criterion chosen from type of operation requiring transmission of the signals and type of information being sent via the signals. For example, the type of operation can be chosen from sending a medical device control command, setting a medical device configuration parameter, requesting medical device status data, requesting medical device log data, requesting secure data from the medical device, and transmitting data to the one or more other devices. The processing device is configured to employ the first communication protocol to perform the type of operation chosen from sending a medical device control command, setting a medical device configuration parameter, and requesting secure data from the medical device, and to employ the second communication protocol to perform the type of operation chosen from requesting medical device status data, requesting medical device log data, and transmitting data to the one or more other devices.

In accordance with aspects of illustrative embodiments, the one or more other devices are selected from the group consisting of a smart watch, a portable monitoring device, a Bluetooth®-enabled wristband device, a blood glucose monitor, a carbohydrate tracking device, and a physical exercise tracking device.

In accordance with aspects of illustrative embodiments, the device further comprises a user interface comprising a graphical user interface (GUI) connected to the processing device. The processing device is configured to display on the GUI at least one screen indicating device application icons corresponding to smartphone applications chosen from a medical device operation application, a blood glucose monitor application, a carbohydrate tracking application, and a physical exercise tracking application, a medication delivery management application, and an integrated disease management application, and at least one application configuration prompt for a user selected setting chosen from Bluetooth® enabled and Bluetooth® disabled for each of the smartphone applications.

In accordance with illustrative embodiments, a medical device is provided that comprises a radio frequency (RF) circuit configured to exchange RF signals with one or more devices different from the medical device, a memory device; and a processing device connected to the RF circuit and the memory device and configured to employ a selected one of at least two wireless communication protocols to exchange, via the RF circuit, RF signals with the one or more devices, wherein the at least two wireless communication protocols comprises a first communication protocol that is employed by the processing device to pair the medical device with the one or more devices to securely exchange secure information chosen from configuration data, medical device operation data, and control signals to operate the medical device, and a second communication protocol that is employed by the processing device to pair the medical device with the one or more devices to send information chosen from medical device data and notifications that requires less security than the secure information to the one or more devices.

In accordance with aspects of illustrative embodiments, the one or more devices is selected from the group of a handheld, dedicated controller for the medical device, and a smartphone having a medical device control app stored thereon for execution to control the medical device.

In accordance with aspects of illustrative embodiments, the first communication protocol limits pairing of the medical device to only a selected one of the one or more devices for controlling operations of the medical device.

In accordance with aspects of illustrative embodiments, the first communication protocol is a Bluetooth® Low Energy (BLE) communication protocol. For example, the BLE communication protocol has no broadcast mode.

In accordance with aspects of illustrative embodiments, the first communication protocol is specific to the medical device and the selected one of the one or more devices and not usable by remaining ones of the one or more other devices to pair with the medical device.

In accordance with aspects of illustrative embodiments, the second communication protocol is a standard Bluetooth® protocol that is employed by the medical device to pair with the one or more other devices and comprises a broadcast mode to discover the one or more other devices.

Additional and/or other aspects and advantages of illustrative embodiments will be set forth in the description that follows, or will be apparent from the description, or may be learned by practice of the invention. The present invention may comprise devices to be paired and methods for operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of example embodiments will be more readily appreciated from the following detailed description, taken in conjunction with the accompanying drawings, of which:

FIG. 1 depicts a medical device and a controller in accordance with an illustrative embodiment;

FIGS. 2A, 2B and 2C are block diagrams, respectively, of the medical device and the controller of FIG. 1 and of another device in accordance with an illustrative embodiment;

FIGS. 6A, 6B and 7 illustrate a first use case of a medical device paired with a controller and the controller paired with another device in accordance with an illustrative embodiment;

FIGS. 8A, 8B, 8C, 8D and 8E are example graphical user interface screens of the controller of FIGS. 6A, 6B and 7 in accordance with an illustrative embodiment;

FIGS. 15, 16, 17, 18, 19, 20, 21, 22, and 23 are example graphical user interface screens of an Integrated Disease Management (IDM) app on a smartphone.

Throughout the drawing figures, like reference numbers will be understood to refer to like elements, features and structures.

DETAILED DESCRIPTION OF ILLUSTRATIVE EMBODIMENTS

Figure 2A:
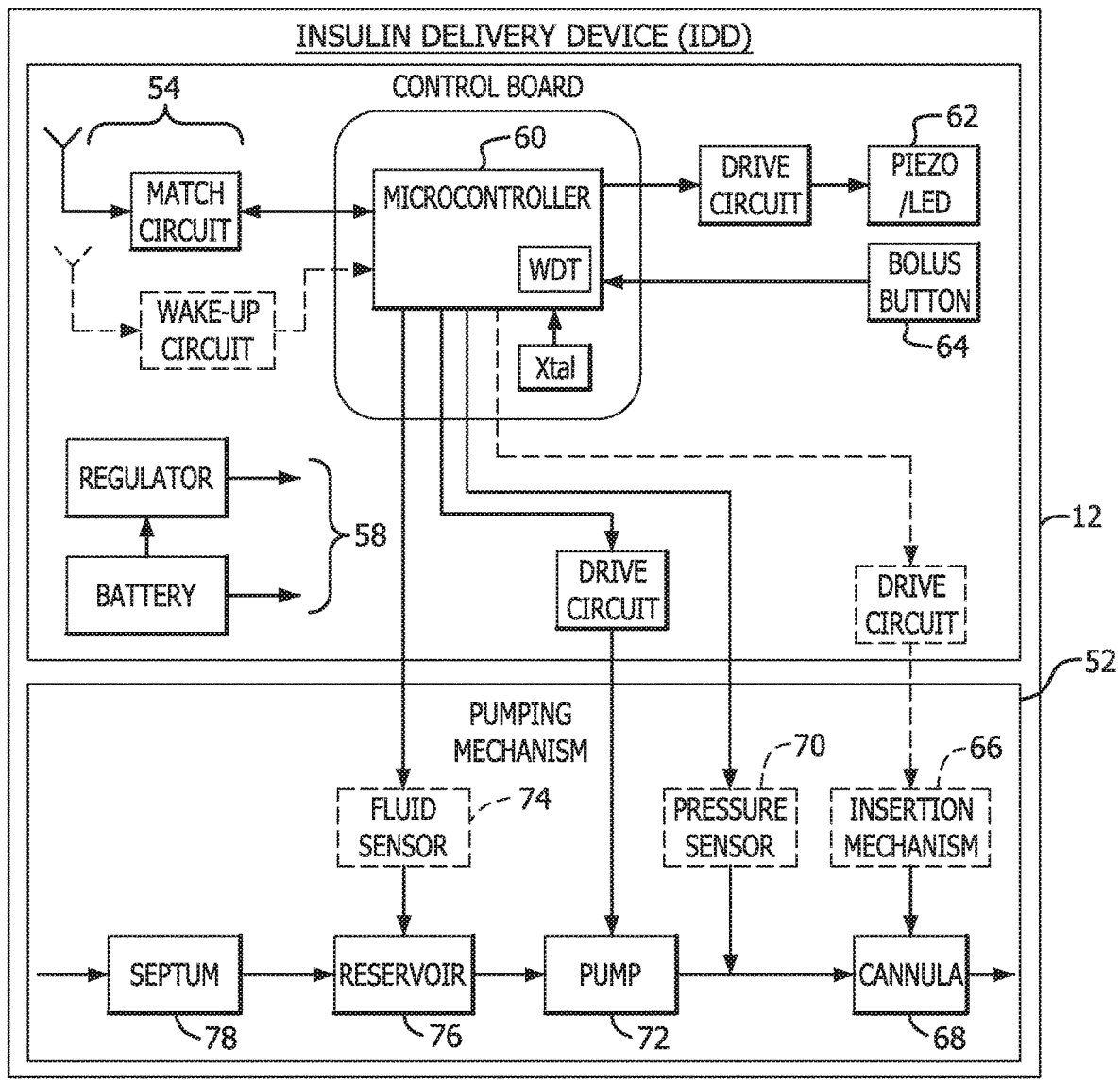

Reference will now be made in detail to example embodiments, which are illustrated in the accompanying drawings.

Problems are overcome and advantages are realized, by illustrative embodiments described below wherein a wearable medical device securely communicates with another device to avoid undesirable MUM eavesdropping or takeover. Further, illustrative embodiments described below minimize the likelihood of personal data privacy breaches when a medical device communicates with one or more other devices.

With reference to FIG. 1, an illustrative medication delivery system 10 is shown having a wearable medical device 12, and a controller 14 with display 24 or other user interface. As will be described herein and in accordance with illustrative embodiments, the medical device 12 can be used with a dedicated controller 14 or with a smartphone with an app 14 configured to operate as a controller 14, and the medical device can also be connected via its controller 14 to other devices 16 or smartphone apps 16 that provide additional functions, described below in connection with an illustrative first use case (e.g., FIGS. 6A, 6B and 7) and an illustrative second use case (e.g., FIGS. 10 and 11). These other devices 16 or smartphone apps 16 can be related, for example, to one or more BAN devices such as a blood glucose meter, smart watch, exercise monitor, and the like as shown in the example Integrated Disease Management (IDM) system depicted in FIG. 14. The medical device 12, the dedicated wireless controller (WC) 14 or device control app 14 in a smartphone, and the other devices 16 or smartphone apps 16 that provide additional functions (e.g., IDM functions), are configured to have communication links with each other and optionally with additional devices in a LAN, WAN or internet cloud, while minimizing likelihood of personal data privacy breaches, and MITM and eavesdropping attacks such as nefarious attacks or unintended interference wherein control of the medical device 12 is undesirably altered by another device. For example, as described below in connection with illustrative embodiments, the medical device 12 and the controller 14 can employ a secure, BLE-based intradevice communication protocol for secure control operations such as medication delivery, and a standard interdevice Bluetooth® protocol (e.g., legacy Classic Bluetooth®) can be used for pairing the medical device 12 with controller device 14 and/or devices 16 (e.g., Bluetooth® earpieces or smart watches) that are merely exchanging information (e.g., status data or log data or delivered drug amounts) but not controlling the medical device 12 configuration or dosing operations (e.g., not specifying or setting bolus amounts, or initiating and terminating pump delivery operations).

The medical device 12 can be, for example, a disposable insulin delivery device (IDD) 12 for single patient use that is configured for continuous subcutaneous delivery of insulin at set and variable basal (24-hour period) rates and bolus (on-demand) doses for the management of patients with Type 2 Diabetes Mellitus (T2DM) requiring insulin therapy. It is to be understood, however, that the medical device 12 can be any on-body medical device (e.g., wearable infusion pump or continuous glucose meter) or BAN medical device (e.g., handheld blood glucose meter, smartphone with medical condition management apps, dedicated wireless controller for on-body device, smart watch, or wearable fitness and health monitor). It also is to be understood, however, that the medical device 12 can be used for other applications besides fluid delivery and, if the medical device 12 is a medication delivery device, it can be used to deliver any type of fluid and is not limited to insulin delivery.

The IDD 12 addresses an unmet need for many Type 2 patients on multiple daily injections (MDI) requiring a discreet, simple and cost effective insulin delivery alternative to the traditional complex insulin pump. With continued reference to FIGS. 1, 2A and 2B, the IDD 12 is part of a system 10 that is an advanced insulin delivery system for use by patients with T2DM. The IDD 12 is configured for 24-hour-a-day use in all environments typically inhabited by the target users. The IDD 12 is configured to allow the patient user to wear the IDD for a period of three days (up to 84 hours). The IDD 12 has four (4) main functions: delivering user-set daily basal insulin rate; delivering user-set bolus insulin amount; delivering manual bolus insulin dose(s); and generating system status and notifications. As described below, the IDD 12 communicates wirelessly with its controller (i.e., hereinafter referred to as the wireless controller (WC 14)) through a Bluetooth® Low Energy (BLE) interface. In addition to IDD operational data, the IDD 12 sends feedback to the WC 14 if it detects issues with the IDD (e.g., memory corruption, low or empty reservoir). The WC 14 is configured to program the IDD 12 to deliver a daily basal insulin rate and bolus or food dose insulin amount to the patient. The WC 14 is configured to also provide status information about the system 10. The WC 14 also enables connectivity to a BLE Wireless Connected Device Interface (BWCDI) of an external device 16 for data exchange. As such, WC 14 can have an optional function of enabling IDD 12 data to be sent to an external device 16 via a BWCDI.

In the illustrated embodiment shown in FIG. 2A, the IDD 12 has a microcontroller 60 configured to control a pumping mechanism 52, wireless communication with the WC (e.g., via an RF circuit 54 having a match circuit and antenna), and pump operations. The IDD has a bolus button(s) 64 for manual delivery of medication in addition to programmed delivery of medication. The pumping mechanism 52 comprises a reservoir 76 for storing a fluid medication (e.g., insulin) to be delivered via a cannula 68 to the patient wearing the IDD, and a pump 72 for controllably delivering designated amounts of medication from the reservoir through the cannula. The reservoir 76 can be filled via a septum 78 using a syringe. The IDD has a manual insertion mechanism 66 for inserting the cannula 68 into a patient; however, the processor 60 can be configured to operate an optional drive circuit to automate operation of the insertion mechanism 66 to deploy the cannula 68 into the patient. Further, the IDD 12 can be optionally provided with a fluid sensor 74 or a pressure sensor 70 for occlusion detection, for example. An LED 62 can be operated by the microcontroller 60 to be on or flash during one or more pump operations such as during reservoir priming, for example. The IDD 12 is powered by a battery and regulator as indicated at 58. When initializing the IDD 12 (e.g., powering on to begin pairing with the WC 12), the bolus button(s) 64 can be configured as wake-up button(s) that, when activated by the user, causes the IDD 12 to wake from a power conserving shelf mode.

Figure 2B:
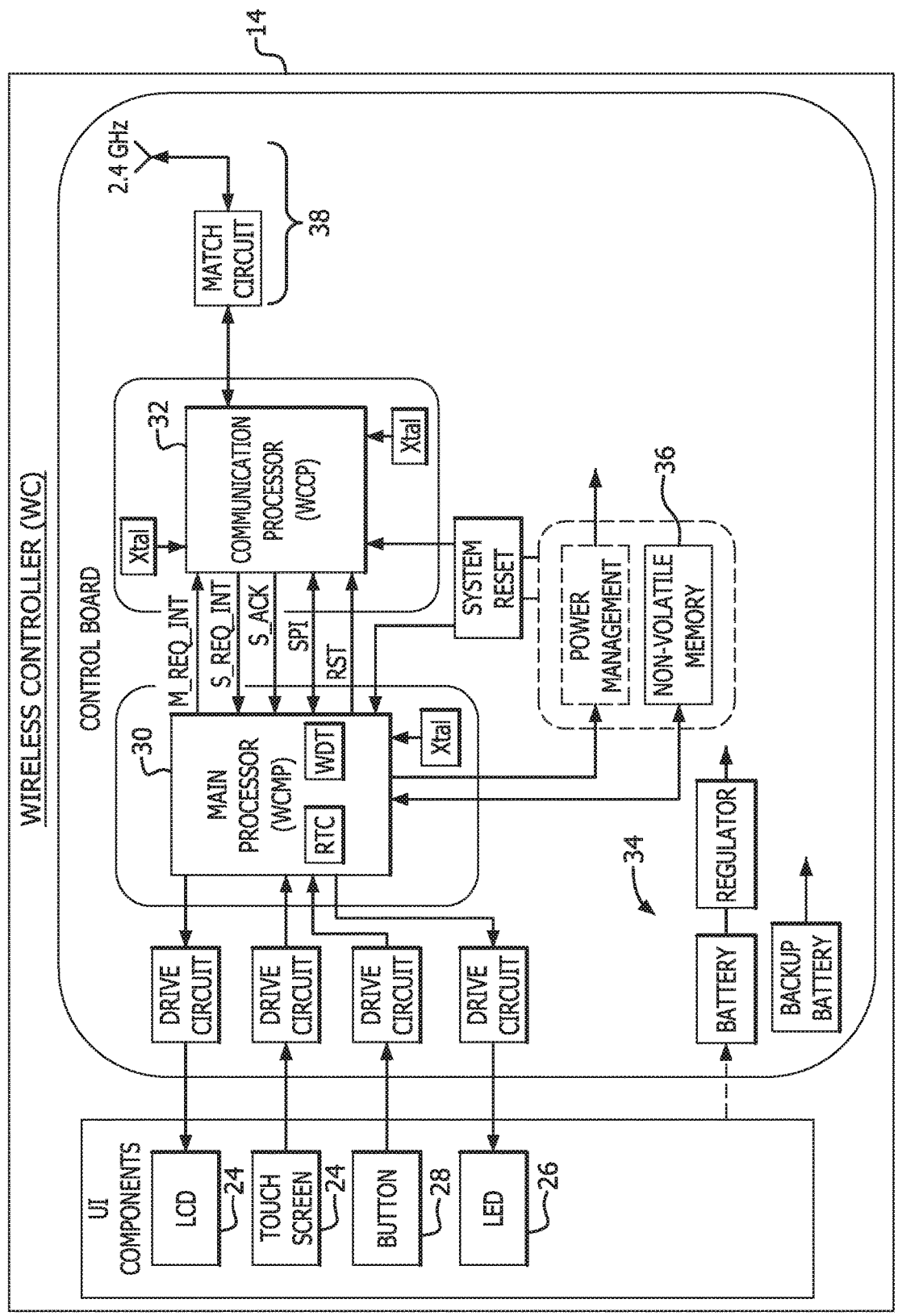

In the illustrated embodiment shown in FIG. 2B, the WC 14 can be implemented as a dual microprocessor component having: 1) a WC Main Processor (WCMP) 30, and a WC Communications Processor (WCCP) 32. It is to be understood, however, that the WC 14 can be configured as a single processor device. The two processors 30, 32 communicate with each other through a serial peripheral interface (SPI). The two processors 30, 32 can also interrupt each other through two interrupt pins, M_REQ_INT and S_REQ_INT.

With reference to FIG. 2B, the WCMP 30 is connected to the user interface (UI) components such as the LCD display with touch screen 24, one or more buttons 28, optional indicator 26 (e.g., speaker, vibration circuit, LED, buzzer), and the like. The WCCP 32 is connected to radio frequency (RF) components 38 (e.g., an antenna and a match circuit)

and is mainly responsible for the WC 14's wireless communication with the IDD 12. It is to be understood, however, that the RF components 38 can comprise one or more antennas and related circuitry to communicate with other devices 16 via different communication protocols. The WC 14 is designed to be non-field serviceable (i.e. no parts to be inspected, adjusted, replaced or maintained by the user), except for replaceable alkaline batteries 34 for power. A non-volatile memory (e.g., FLASH memory) 36 is provided in the WC to store delivery and status data received from the IDD 12 such as delivery dates and times and amounts.

With continued reference to FIG. 2B, the LCD with capacitive touch screen 24 serves as the visual interface for the user by rendering visual and graphical outputs to the user (e.g., system information, instructions, visual notices, user configurations, data outputs, etc.), and by providing a visual interface for the user to enter inputs (e.g., device operation inputs such as IDD pairing and set up and dosing, and configuration parameters, and so on). The WC display with capacitive touch screen 24 detects at least single-touch gestures over its display area. For example, the touch screen is configured for recognizing user tactile inputs (tap, swipe, and button press), allowing for navigation within UI screens and applications. The touch screen 24 aids in executing specific system functionalities (i.e. IDD 12 setup and pairing with the WC 14, insulin dosing, providing user with dosing history, and IDD deactivation and replacement with another IDD, and so on) through specific user interactions. The WC 14 can also include a button 28 such as a device wake-up button that, when activated by the user, causes the WC 14 to wake from a power conserving sleep mode. The WC 14 can also have an LED 26 to indicate low battery status (e.g., indicate low battery state when there is 12 hours or less of usage remaining).

The WC 14 radio frequency (RF) interface with the IDD 12 is, for example, based on a Bluetooth® Low Energy or BLE-based communication protocol, although other wireless communication protocols can be used. In the example medication delivery system 10, the WC 14 and IDD 12 communicate wirelessly within a distance of up to 10 feet or approximately 3 meters, utilizing the ISM band from 2400 MHz to 2480 MHZ spectrum. The WC 14 communicates with the IDD 12 while the IDD is adhered to the body in open air. The WC 14 is the central device or master, and the IDD 12 is the peripheral device or slave. Whenever the WCMP 30 wants to send information to the IDD 12 or retrieve information from the IDD 12, it does so by interacting with the WCCP 32, which in turn, communicates with the IDD 12 across the BLE link via the respective RF circuits 54 and 38, as shown in FIGS. 2A and 2B respectively.

FIG. 2C is a block diagram depicting an example device 16. The device 16 can be a smartphone, smart watch, Bluetooth®-enabled health and/or fitness monitoring device, Bluetooth®-enabled headset or earpiece, among other Bluetooth®-enabled wireless devices 16, for example. The device 16 comprises a processor and memory 80 that can be integrated or separate components. The device 16 can have a Bluetooth®-enabled wireless communications interface 84 and an optional cellular communications interface 82, for example. The device 16 can also have different user interfaces such as one or more of a microphone 88, touchscreen 86 or keypad or other user input device, an audio signal output device (e.g., speaker or buzzer) 90, and/or a vibration circuit 92. The WC 14 communicates with the device 16 across a BLE link, for example, via respective RF circuits and BLE wireless interfaces.

In accordance with an aspect of illustrative embodiments, the WC 14 (e.g., its WCCP 32) and the IDD 12 can communicate in accordance with a specific intradevice pairing protocol and various operations to mitigate risk that the WC 14 pairs with an unintended IDD 12' or, vice versa, that an intended IDD 12 pairs with an unintended WC 14' as described, for example, in commonly owned PCT published applications WO 2018/183036 and WO 2018/183038, which are incorporated herein by reference. As defined herein, "intradevice" refers to the WC 14 being paired with and bonded with one particular medical device 12 (e.g., IDD 12). Either unintended pairing scenario could cause unintended operation or control of the pumping mechanism 52, potentially resulting in insulin over-infusion that can be injurious to the patient. In accordance with another aspect of illustrative embodiments, the WC 14 can also communicate with another device(s) 16 in accordance with a more ubiquitous interdevice communication protocol (e.g., a protocol that is more commonly used by different commercially available devices 16), to enable the WC 14 to send less sensitive data than medical device control commands to various devices 16. As defined herein, "interdevice" refers to the WC 14 being able to send selected IDD 12 information with one or more other devices 16.

For example, Bluetooth® Low Energy (BLE), marketed as Bluetooth® Smart, is a wireless technology for establishing packet-based wireless networks among wireless devices operating in the 2.4 GHz to 2.4835 GHz frequency range with significantly reduced power consumption compared to legacy Bluetooth® devices, which are sometimes referred to as Classic Bluetooth® devices. Low power wireless devices compliant with the Bluetooth® Smart specification are advantageous for healthcare applications because they are expected to run for long periods of time on a button or coin battery. Bluetooth® Smart Ready devices are wireless devices with dual protocol stacks capable of communicating with legacy Classic Bluetooth® devices, as well as Bluetooth® Smart devices. For example, a smartphone with IDD control app 16 can have Bluetooth® Smart Ready operation so that it can communicate with a legacy Classic Bluetooth® device 16 such as an activity monitor or continuous glucose monitor (CGM), as well as a personal device such as an IDD 12 having Bluetooth® Smart operation to allow for pairing using, for example, the specific intradevice pairing protocol to restrict which device 14 the IDD 12 can exchange pump operation data with and receive control commands from.

Figure 3:
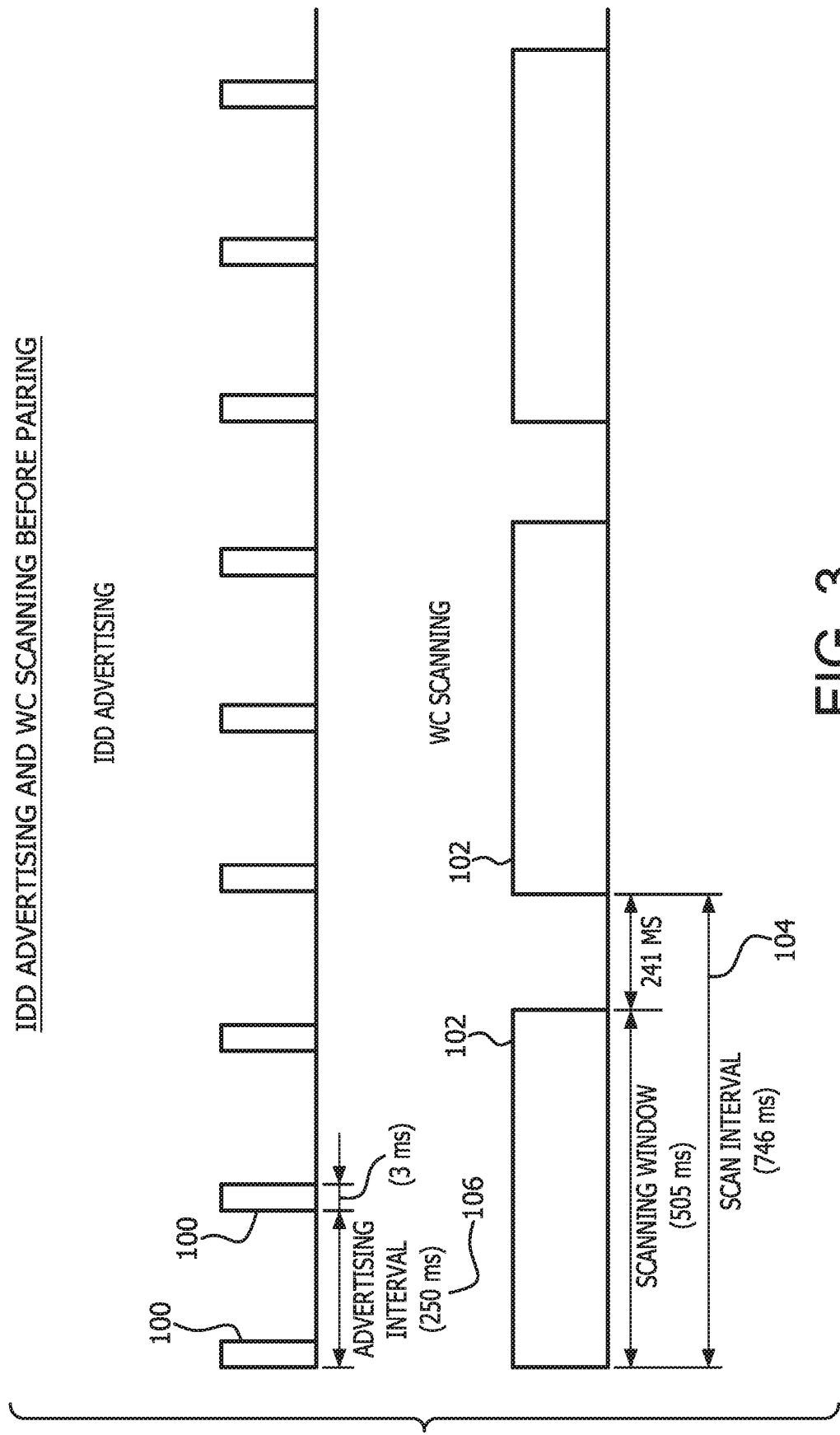
FIGS. 3, 4 and 5 are diagrams of example signals transmitted from the medical device and example scanning windows of the controller in accordance with an illustrative embodiment.
Figure 4:
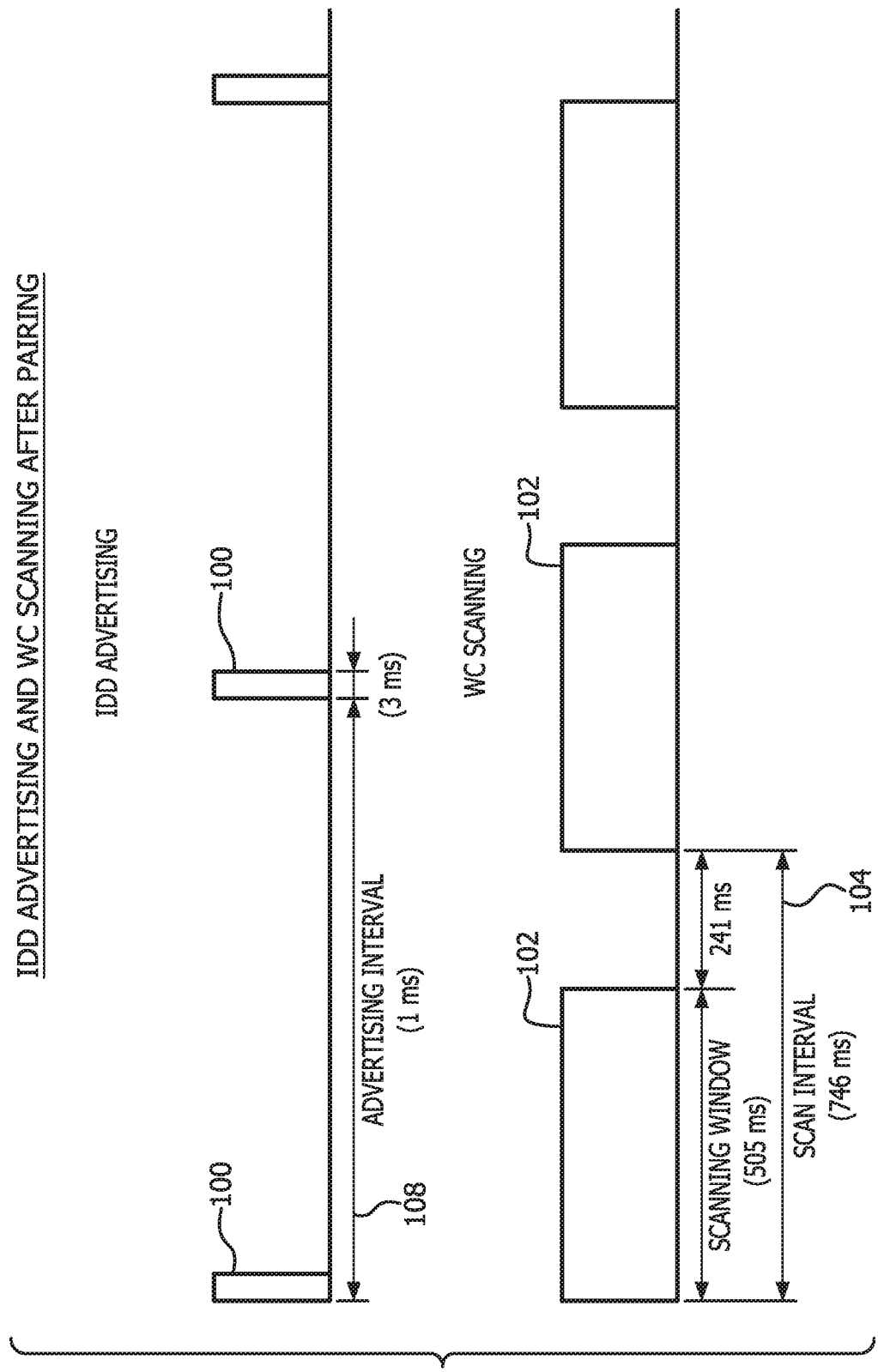
Figure 5:
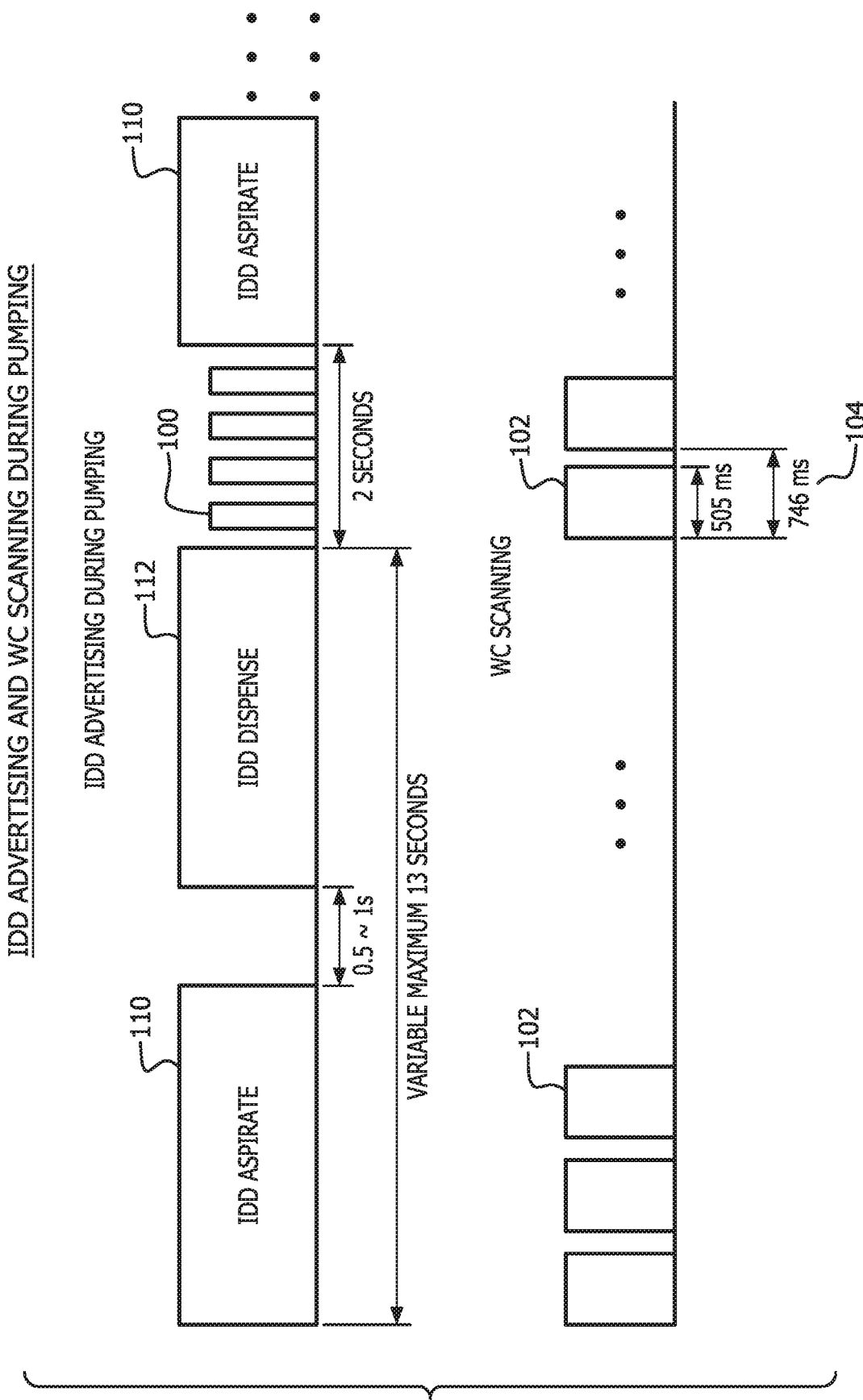

An illustrative example of a specific intradevice pairing protocol for pairing the IDD 12 with the WC 14 will now be described with reference to FIGS. 3, 4 and 5. In accordance with an illustrative embodiment and as described below, the intradevice pairing protocol has particular advertising and scanning window durations, and corresponding intradevice pairing software is provided to the IDD 12 and WC 14 for a secure, bonded relationship. It is to be understood that the timing described with reference to FIGS. 3, 4 and 5 is for illustrative purposes and that timing specifications can be different depending on the design and inputs used for a particular device pairing application. As will also be discussed below, an interdevice, legacy Classic Bluetooth® pairing protocol available to, and commonly used among, various devices 16 can be also used instead for communications requiring less security than, for example, control communications for a delivery device and therefore no bonded relationship as between the IDD 12 and WC 14.

Example IDD 12 advertising and WC 14 scanning before intradevice pairing are illustrated FIG. 3. Upon waking up and before pairing, every 250 ms (+/−10%) as indicated at 106, the IDD 12 advertises with IDD Startup Advertising Data packets 100, and waits for 3 ms (+/−10%) for the possible reply from a WC 14. At the WCMP 30's request, the WCCP 32 initiates the communication by starting scanning the IDD advertisement every 746 ms (+/−10%) 104 for about a 505 ms (+/−10%) scanning window 102. At the end of the scanning time period 104, if the WCCP 32 does not detect any advertising packet 100 within a transport layer timeout period, the WCCP stops scanning and sends a Nack response with a Transmission Timeout error code. The WCCP 32 goes to sleep i not advertising is detected.

The WC 14 can determine if a particular type of device 12 is in its vicinity. For example, the IDD 12 Startup Advertising Data can comprise IDD identifying information (e.g., selected dynamic and/or static parameters or values that identify a type of device such as manufacturer and/or model or other characteristic) such that the WC 14 can be configured to only pair with devices or IDDs having designated IDD identifying information and not with other devices that do have the designated IDD identifying information. Thus, if the WCCP 32 determines that the IDD 12 Startup Advertising Data has IDD identifying information relating, for example, to its particular manufacturer, the WC 14 can pair with the advertising IDD 12. If not, the WCCP 32 continues scanning.

Example IDD 12 advertising and WC 14 scanning after pairing are illustrated FIG. 4. After intradevice pairing, and optionally when the IDD 12 is not actively pumping, the IDD advertises with a IDD Periodic Data Packet 100 at a selected interval 108 (e.g., every 1 second (+/−10%)). The IDD Periodic Data Packet can be provided with an alert code or other data indicating a condition requiring generation of a notification to the user(s) or otherwise indicating a request for notification. After each advertisement 100, the IDD 12 waits for 30 ms (+/−10%) for the possible reply from the WC 14. After pairing, at the WCMP 30's request, the WCCP 32 initiates the communication by starting scanning the IDD advertisement every 746 ms (+/−10%) 104 for a 505 ms (+/−10%) scanning window 102.

Example IDD 12 advertising and WC 14 scanning during pumping are illustrated in FIG. 5. If the IDD 12 is delivering a medication such as insulin, it can optionally advertise every 500 ms for 2 seconds at the end of a dispense stroke 112. Even though it is not indicated in FIG. 6, during the break time between IDD aspirate periods 110 and dispense periods 112, the IDD 12 still tries advertising if possible. When the IDD 12 is pumping, at the WCMP 30's request, the WCCP 32 initiates the communication by starting scanning the IDD advertisement every 746 ms (+/−10%) 104 for 505 ms (+/−10%) scanning windows 102.

In the illustrated example of FIGS. 3, 4 and 5, the intradevice wireless protocol implemented by the WC 14 and its paired IDD 12 configures the IDD 12 to only accept a control command from the paired WC 14 such as a wireless command to deliver insulin or to configure dosage amounts and to only send sensitive device data or information to the paired WC 14. This bonded, specific intradevice communication relationship between the WC 12 and IDD 14 ensures that no other device can control operation of the IDD 12 for safety and security reasons or receive sensitive data or information, and this bonded, specific intradevice communication relationship remains until the IDD is deactivated. After IDD deactivation, the WC 14 is free to pair with a new IDD 12; however, at any given time, the WC 14 is preferably only allowed to pair with one IDD 12. If the WC 14 is a smartphone, as opposed to a dedicated wireless controller, then the smartphone can be configured with a medical device control app 14 that controls the smartphone's pairing and resulting bonded relationship with only one IDD 12 at a time.

It is to be understood, however, that a standard or legacy Classic Bluetooth® protocol can be used by the IDD 12 to pair with the WC or smartphone 14 and optionally pair with another device 16 (e.g., a smart watch or Bluetooth®-enabled headset or earpiece), or can be used by the WC 14 to pair with another device 16, to merely exchange medical device status or log data that does not require the same bonding relationship limitation of intradevice pairing protocol described above in connection with FIGS. 3, 4 and 5. For example, if the IDD 12 is merely using the Bluetooth® link to request that a notification be generated at the WC 14 or other device 16, and therefore the IDD 12 is not sending sensitive IDD operational status data or receiving commands, then a common interdevice protocol (e.g., legacy Classic Bluetooth® can be used for pairing with and requesting notification by another device 14, 16 that also supports the same protocol. To send less sensitive information, such legacy Classic Bluetooth®-enabled connectivity need not limit the device(s) 16 to which the IDD 12 is paired, or require specific, non-standard intervals and therefore does not require software in the IDD 12 and the WC 14 and/or other device 16 that supports a specific intradevice protocol for wireless connectivity having a level of security needed for safe and secure medical device operation. In other words, the IDD 12 and the WC 14 can employ a secure, intradevice BLE-based communication protocol for secure drug delivery control operations, and a common interdevice and standard Bluetooth® protocol (e.g., legacy Classic Bluetooth) can be used for pairing the IDD 12 with devices 14 and/or devices 16 (e.g., Bluetooth® earpieces or smart watches) that are merely receiving requests for notifications about IDD operational problems, or collecting status or log data from the IDD 12.

The medical device 12, dedicated controller 14 and smartphone with medical device controller app 14 are configured to each implement at least two different wireless communication protocols for exchanging, respectively, data or signals characterized as having at least two different levels of security requirements. For example, with reference to FIGS. 2A, 2B and 2C, the RF components 54 in the medical device 12, the RF components 38 in the dedicated controller 14 or similar RF components in the smartphone can comprise antenna(s) and matching circuit(s) as needed to accommodate the two different wireless communication protocols. Similarly, the medical device 12, controller 14 or medical device control app 14 for a smartphone are programmed or otherwise configured to determine when to use the two different wireless communication protocols, depending on the type of operation and the type of information to be exchanged. For example, the medical device 12 and controller or control app 14 are programmed or otherwise configured to constrain medical device configuration and control operations and related data and signals (e.g., set dose amounts, commands to initiate and terminate delivery operation) to communication via the more secure of the two different wireless communication protocols (e.g., a specific intradevice protocol). The data related to configuration and control operations that require more secure communication can be provided with metadata or stored in a designated memory location that signifies that the more secure of the two communication protocols is needed to exchange it between the medical device and the controller or control app 14 and to preclude its communication to a device 16 that does not also employ the same secure wireless protocol such as the specific intradevice protocol. Similarly, device 12 log or history data or notifications that are designated to be less sensitive than device 12 configuration and control data can be provided with metadata or stored in a designated memory location that signifies that the less secure of the two communication protocols can be used to communicate the data from the medical device 12 to the controller or control app 14 and/or device(s) 16 and/or from the controller or control app 14 to the device(s) 16.

Figure 6A:
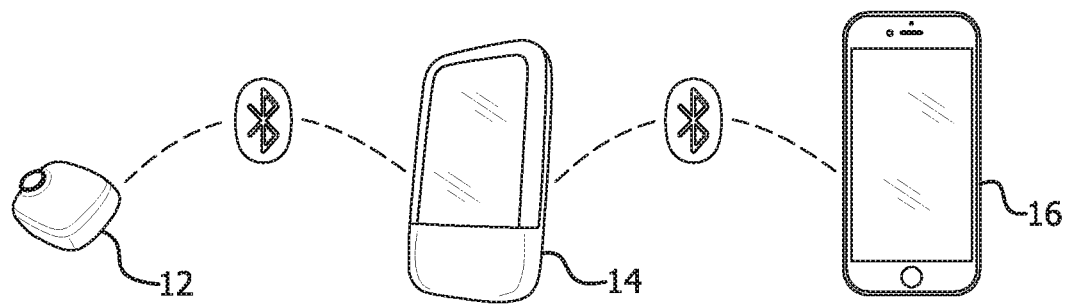
Figure 6B:
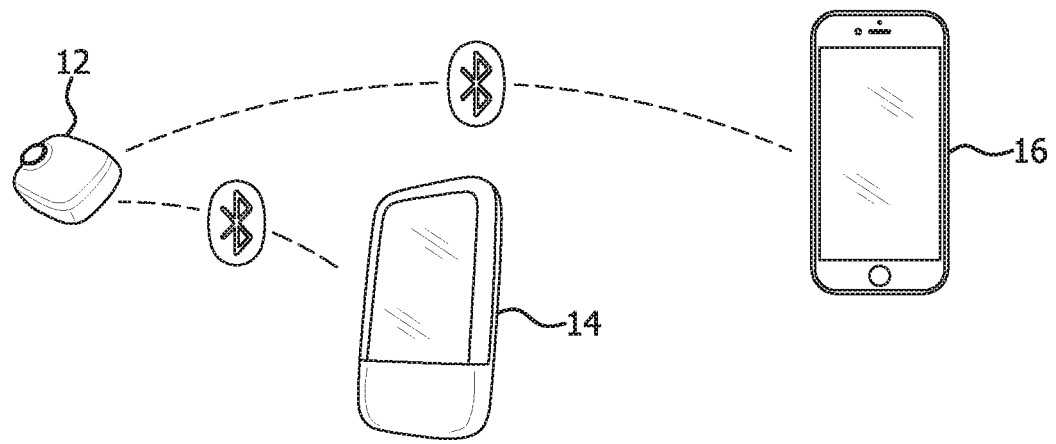

In accordance with an illustrative embodiment and with reference to FIGS. 6A, 6B and 7, a smartphone 16 is configured for use in accordance with an example mobile relay use case or scenario wherein a WC 14 relays selected IDD 12 historical data (e.g., device 12 status or log data) but not real-time operational or control data to a smartphone 16, and the smartphone 16 transmits the relayed information from the WC 14 to device(s) 16 and optionally a cloud-based system 94 but does not participate in the operational control the IDD 12. A number of advantages are realized by enabling the IDD 12 and/or the WC 14 to operate with a smartphone 16. For example, a smartphone 16 can increase storage and connectivity of the IDD 12 and/or the WC 14 by receiving and storing backup files of IDD dosing data or IDD status logs, thereby decreasing the complexity and cost of the IDD 12 and/or the WC 14. In addition, the cellular wireless interface 82 of the smartphone 16 enables the IDD 12 and/or the WC 14 to connect to a wide area network. For example, the smartphone can connect the IDD 12 and/or the WC 14 to cloud computing resource(s) (e.g., a proprietary disease management system via the internet as represented by the cloud 94 in FIG. 7). Thus, smartphone 16 can provide IDD infomatics (e.g., IDD historical bolus dosing amounts) to a Digital Health or other IDM partner, who in turn provides value to customers through connectivity by turning IDD 12 data into actions that benefit users' health. For example, smartphone apps 16 can provide integrated views of IDD 12 data and other disease or patient-related data that can be reviewed by a physician, family, or payer, as well as provide medical condition health coaching. On the other hand, in the illustrative embodiment depicted in FIGS. 6A, 6B and 7, control of the IDD 12 (e.g., configuration and setting of bolus dosing amounts) remains with the WC 14; the smartphone 16 merely receives non-operational IDD 12 information from the WC 14.

With reference to FIG. 7, the IDD 12, WC 14 and smartphone 16 need to be in close proximity to each other to exchange Bluetooth® protocol signals. The WC 14 is a dedicated handheld controller for the IDD 12 that uses intradevice Bluetooth® technology to exchange IDD 12 operational information (e.g., receive IDD 12 status information and provide control signals to the IDD 12), and is configured to pair with and relay a history of IDD 12 data to the smartphone 16 using interdevice Bluetooth® technology. The smartphone 16 can, in turn, push data to a designated cloud-based resource 94 via, for example, WiFi and/or cellular communications. To achieve this additional operation, the WC 14 can be provided with a Bluetooth® transponder and antenna and programmable logic operations to engage in interdevice communications via standard protocols such as legacy Classic Bluetooth®, in addition to the aforementioned circuitry and programmable logic operations used to engage in communications between the IDD 12 and WC 14 using intradevice Bluetooth® technology. The IDD 12 is likewise provided with a Bluetooth® transponder and programmable logic operations to add a broadcast mode to participate in interdevice communications with devices (16) directly as shown in FIG. 6B or indirectly via the WC 14 as shown in FIGS. 6A and 6B.

Example IDD 12 operational information transmitted by the WC 14 to the IDD 12 can be, but is not limited to, basal rate, bolus dose (i.e., food dose) volume, bolus delivery cancel command and device status inquiry. Example IDD 12 operational information transmitted by the IDD 12 to the WC 14 can be, but is not limited to, time and amount of reservoir fluid (e.g., insulin) delivered, activations of bolus button 64, reservoir empty signal and IDD status and error states. As stated above, the IDD 12 operational information exchanges between the IDD 12 and WC 14 are secure using an intradevice Bluetooth® technology as described above (e.g., secure pairing via BLE using 32-bit encryption and no open broadcasts).

Figure 8E:
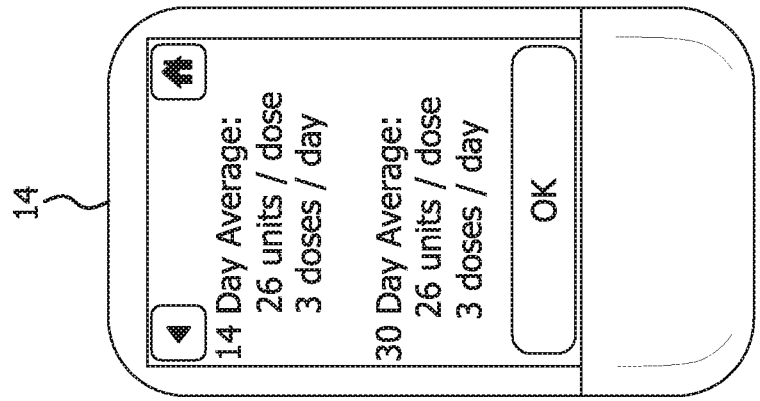
Figure 8D:
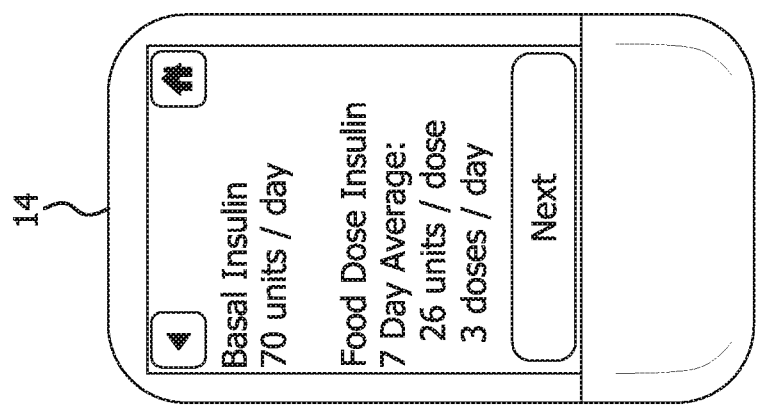
Figure 8C:
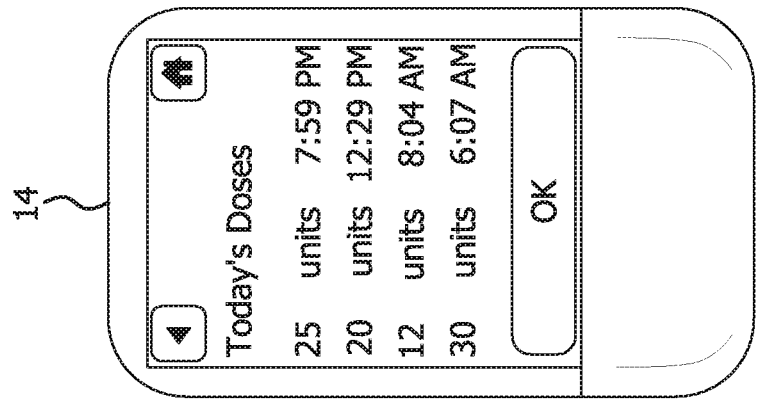

With continued reference to the illustrative embodiment shown in FIGS. 6A, 6B and 7 for the example mobile relay use case, example GUI screens generated on a dedicated handheld WC 14 are depicted in FIGS. 8A through 8E. The WC 14 is programmed to configure the IDD 12 following pairing via the intradevice protocol. For example, the WC 14 can set the food bolus amount to be delivered. The WC 14 also receives status signals from the IDD 12 (e.g., IDD 12 is currently delivering and the delivered amount, reservoir 76 in IDD 12 is near empty or empty, fluid in reservoir 76 of IDD 12 is near expiration or expired, and IDD 12 is experiencing an operational error), and can create a food dose summary based on the delivered amount information, and an IDD Log file (e.g., dates and times for IDD wake up, button 64 press, etc.). FIG. 8A depicts an example IDD Delivering status screen on the WC 14 that can be generated when the WC 14 is receiving IDD 12 status signals indicating that delivery of reservoir 76 fluid is underway. FIG. 8B depicts an example IDD status error screen on the WC 14, whereby the IDD 12 is being deactivated by the WC 14 in response to receiving status signals from the IDD 12 indicating a selected IDD status condition such as an empty reservoir 76 or IDD malfunction. FIGS. 8C, 8D and 8E depict example food dose information screens on the WC 14 that can be generated by the WC 14 using a log of dose delivery information received from the IDD 12.

Figure 9A:
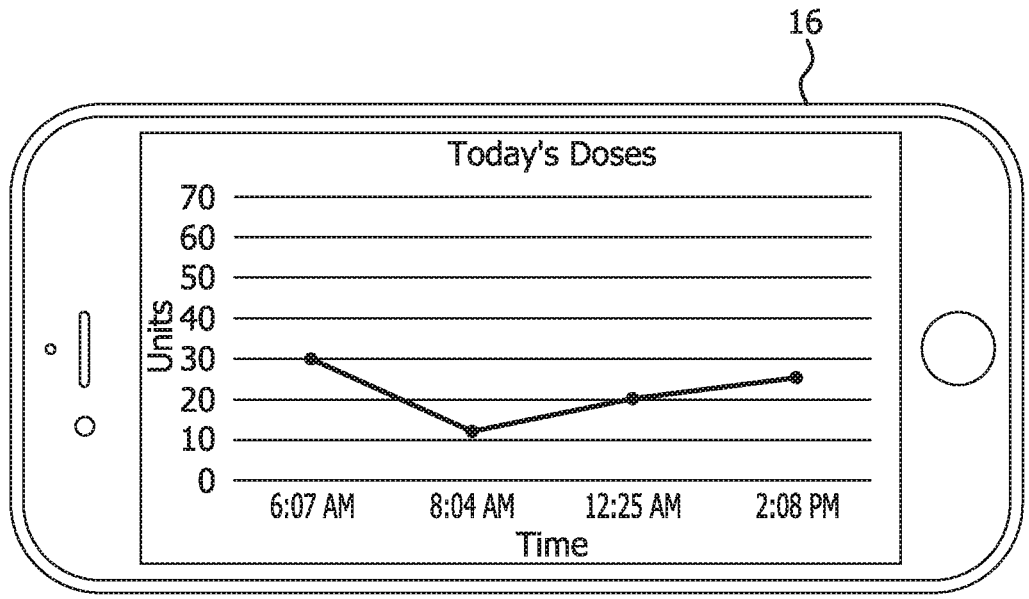
FIGS. 9A and 9B are example graphical user interface screens of the other device of FIGS. 6A, 6B and 7 and of FIGS. 10 and 11 in accordance with an illustrative embodiment.
Figure 9B:
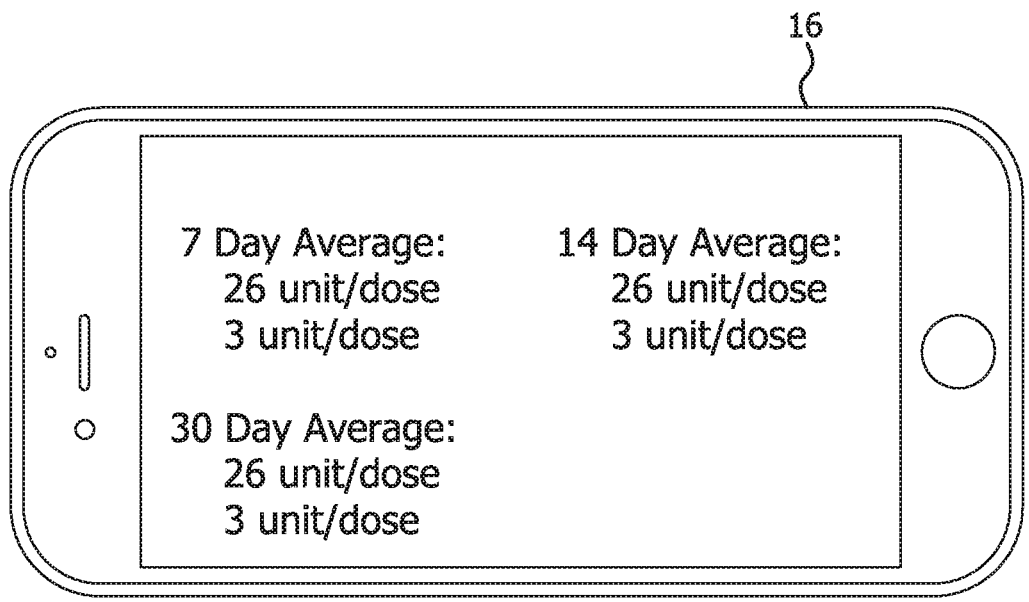

With continued reference to the illustrative embodiment shown in FIGS. 6B, 6B and 7 for the example mobile relay use case, example GUI screens generated on a smartphone 16 are depicted in FIGS. 9A and 9B. The smartphone 16 can receive dosing history data, but does not exchange IDD operational information with the WC 14 or IDD 12 such as sending status inquiries or configuration data or delivery cancel commands to the IDD 12. For example, the smartphone 16 can generate screens such as the food dose summary screens shown in FIGS. 9A and 9B using the history received from the WC 14, but does not generate screens using any of the real-time IDD operational information. For example, the daily doses (e.g., FIG. 8A) can be used to generate the daily dose plot in the smartphone 16 screen in FIG. 9A, and the 7, 14 and 30-day averages (e.g., FIGS. 8B and 8C) received from the WC 14 can be used to generate the 7, 14 and 30-day averages in the smartphone 16 screen in FIG. 9B.

Figure 10:
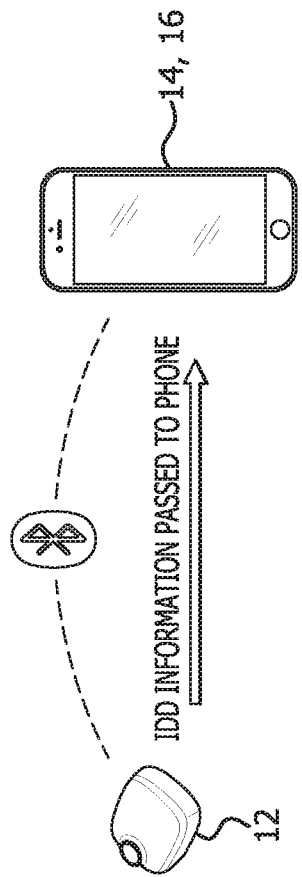
FIGS. 10 and 11 illustrate a second use case of a medical device paired with a controller that is a smartphone and that can be paired with another device in accordance with an illustrative embodiment.
Figure 11:
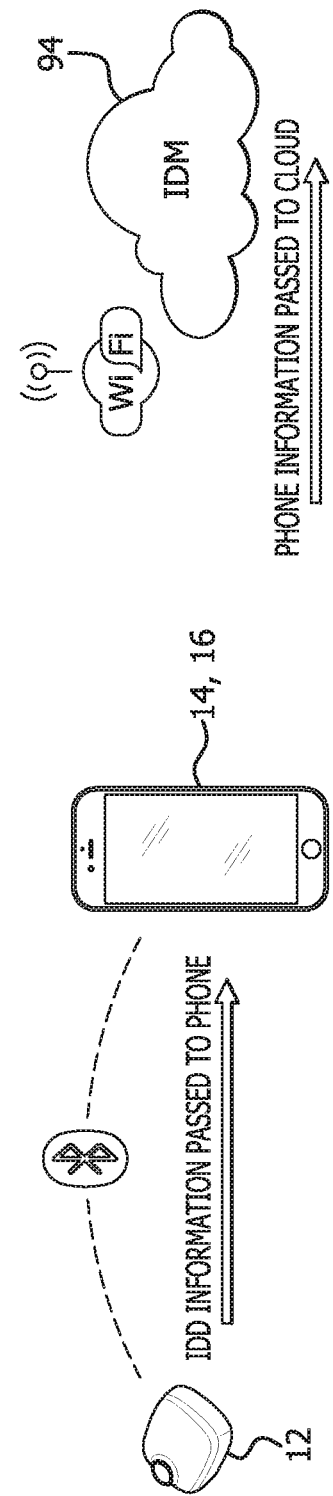
Figure 12B:
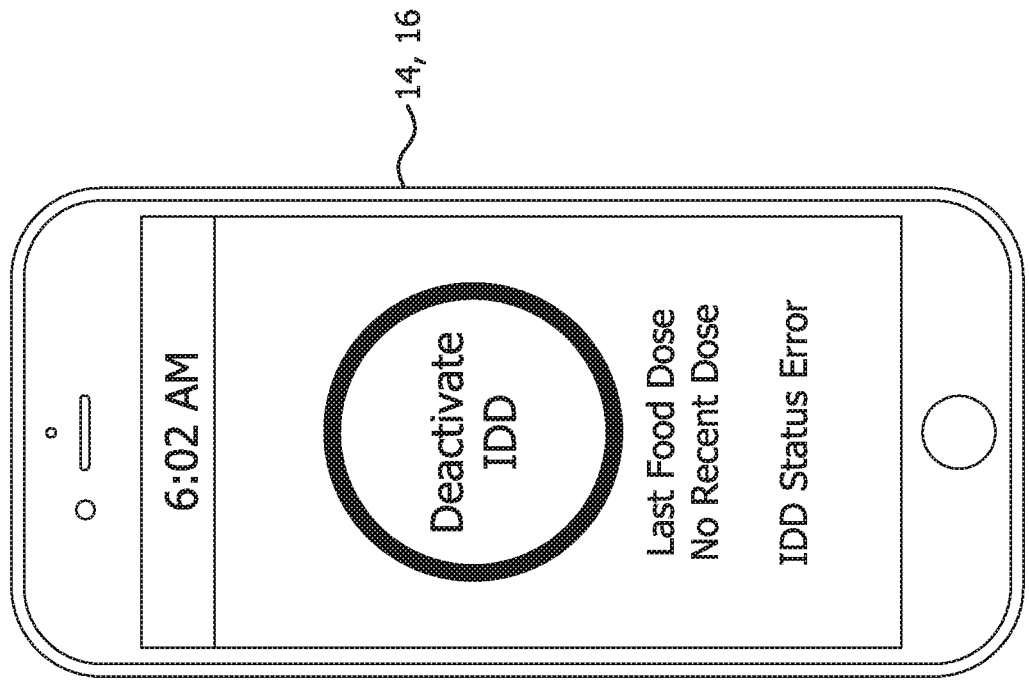
FIGS. 12A, 12B, 12C, 12D and 12E are example graphical user interface screens of the controller of FIGS. 10 and 11 in accordance with an illustrative embodiment.
Figure 12A:
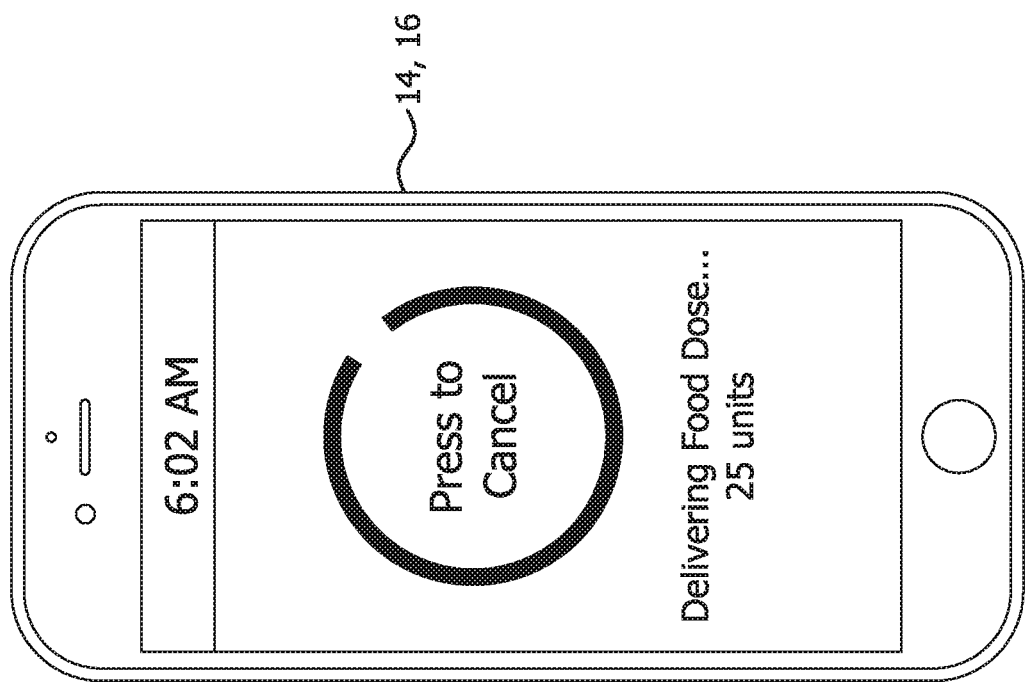
Figure 12E:
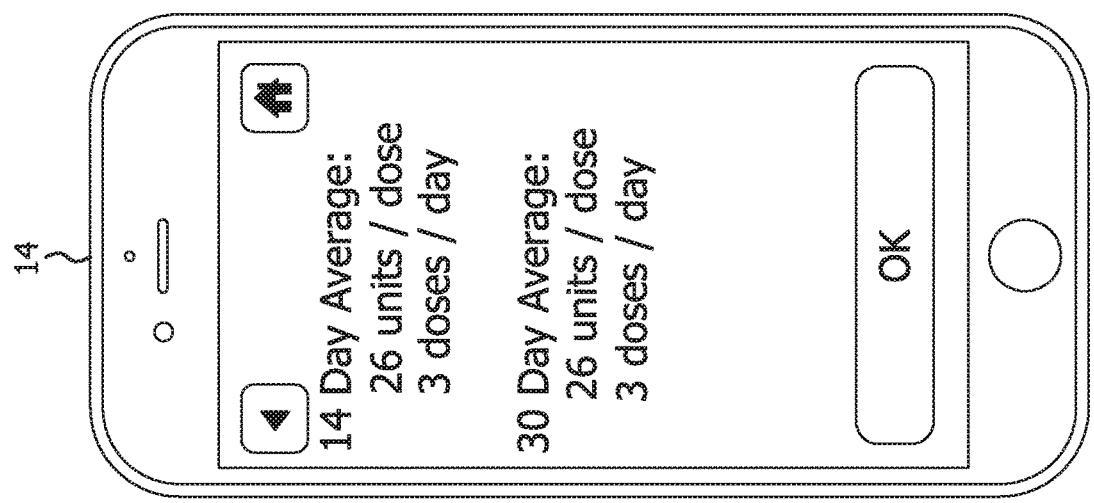
Figure 12D:
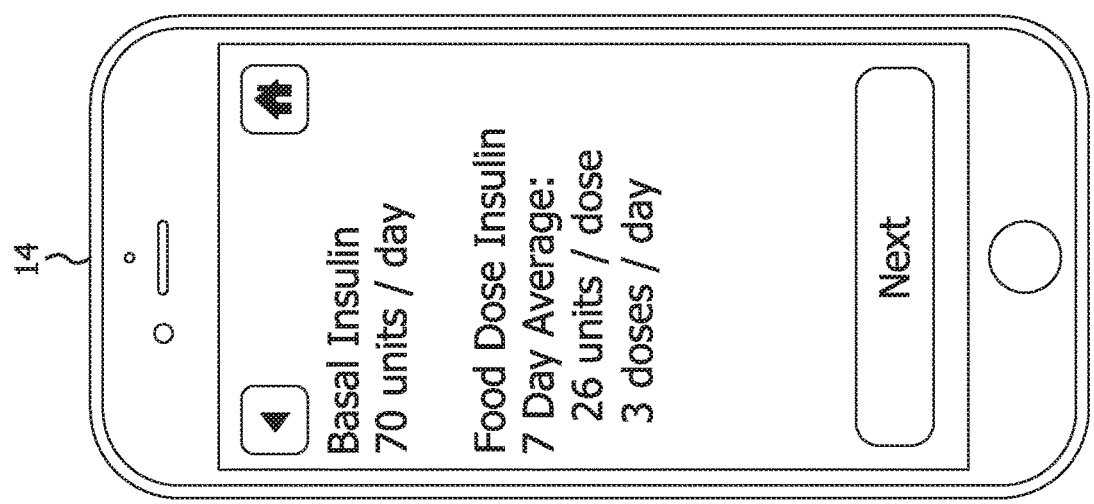
Figure 12C:
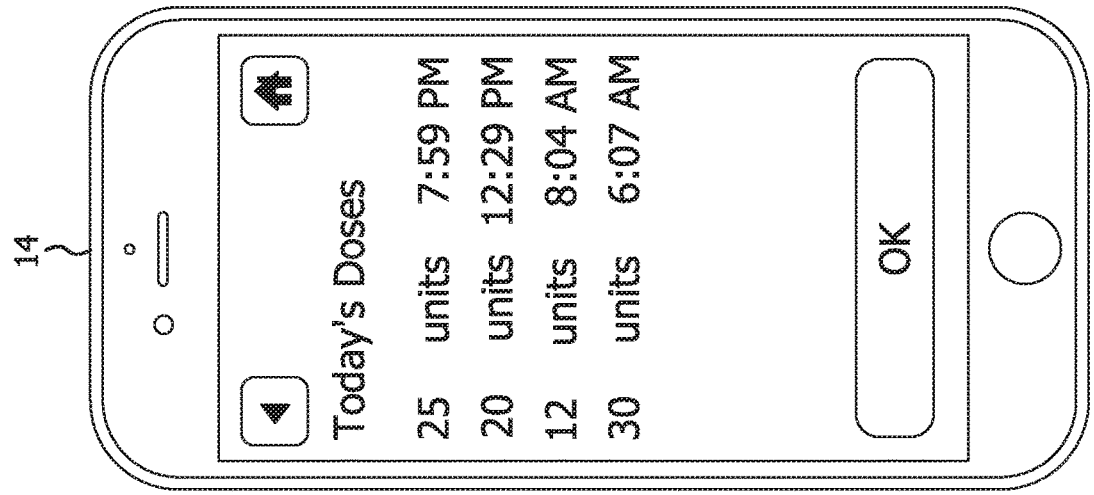

In accordance with another illustrative embodiment and with reference to FIGS. 10 and 11, a smartphone 16 is configured for use in accordance with an example mobile controller use case or scenario wherein the smartphone 16 operates as a WC 14 (i.e., participates in the operational control the IDD 12 using exchanges of real-time operational data with an IDD 12), and the smartphone 16 can transmit less sensitive information than the IDD 12 operational information to other device(s) 16 and optionally to a cloud-based system 94. In other words, the smartphone 16 is provided with WC operational control operations of the IDD 12 in a medical device control app 14 (e.g., available for iPhone and/or Android), as well as be programmed to push IDD 12 data to device(s) 16 or a documented interface (e.g., a cloud). The medical device control app 14 controls the smartphone 16 to perform operational information exchanges with the IDD 12 that are secure using an intradevice Bluetooth® technology as described above (e.g., secure pairing via BLE using 32-bit encryption and no open broadcasts). The smartphone is also configured to use a different interdevice communication protocol (e.g., legacy Classic Bluetooth®) to transmit less sensitive information than the IDD 12 operational information to other device(s) 16 such as the cloud-based system 94. For a medical device control app 16 in the mobile controller use case of FIGS. 10 and 11, example GUI screens generated on a smartphone 16 are depicted in FIGS. 12A through 12E that are similar to the screens shown in FIGS. 8A through 8E except that they are formatted as smartphone GUI screens instead of GUI screens on a dedicated WC 14 that may have proprietary display configuration parameters. For the example mobile controller use case, the smartphone can also generate the screens depicted in FIGS. 9A and 9B.

In accordance with another illustrative embodiment, the smartphone 16 described in connection with FIGS. 6A and 7 (i.e., configured to operate in accordance with the example mobile relay use case) can also be programmed with additional functionality that permits the smartphone 16 user to adjust IDD 12 operational information such as the number of units of insulin to deliver. For example, a user can adjust basal or bolus insulin dosing of the IDD 12 via the WC 14, or indirectly via a smartphone 16 with a medical device control app 14, which can be implemented as described above in connection with the illustrative embodiment depicted in FIGS. 10 and 11 for all or only some of the WC 14 operations (e.g., dose setting) that control the IDD 12. For example, the smartphone 16 employed in accordance with the example mobile controller use case of FIGS. 10 and 11 is configured to employ a communication protocol for secure communications with the WC 14 (e.g., using an intradevice Bluetooth® technology as described above such as secure pairing via BLE using 32-bit encryption and no open broadcasts). The intradevice Bluetooth® technology employed by the smartphone 16's medical device control app 14 to communicate with the WC 14, however, need not have the above-described constraints (e.g., advertising intervals and windows for scanning and IDD power saving as shown in FIGS. 3-5) used for IDD 12 and WC 14 communications. The smartphone 16 is also configured for the mobile relay use case that employs a different interdevice communication protocol (e.g., legacy Classic Bluetooth®) to transmit less sensitive information than the IDD 12 operational information to the cloud-based system 94. For example, in the mobile relay use case, the smartphone 16 can interconnect with LAN/WAN (e.g., using a Bluetooth® or other wireless communication protocol for non-BAN connectivity) to enable cooperation with an interconnected diabetes management (IDM) system such as to pair a smartphone 16 IDM app with patient glucose monitor to track BG levels and insulin dose capture.

Figure 13:
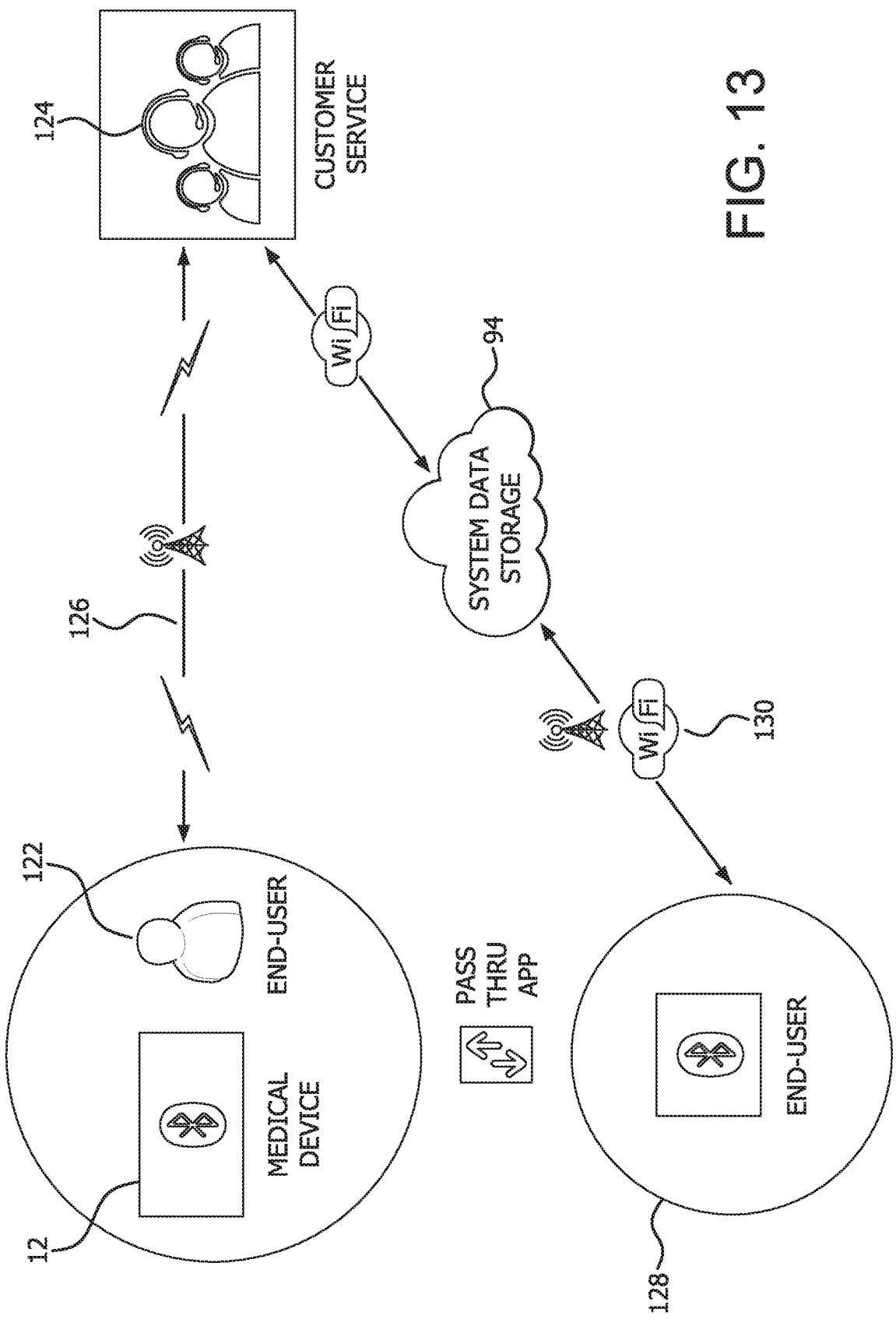
FIG. 13 is a diagram of a secure communication system for sending data from a medical device to a manufacturer, product support team or service customer support personnel for troubleshooting and diagnosis of issues in accordance with an illustrative embodiment.

Another advantage of smartphone connectivity in connection with a medical device 12 (e.g., an IDD) is realized in accordance with another illustrative embodiment and with reference to FIG. 13. Currently, very limited system data (e.g., device 12 data or patient-generated data) from a medical device is available to the manufacturer or a product support team for remote troubleshooting. A customer support mode is typically available to the end user 122 (e.g., via a password) where some information can be relayed to customer service personnel 124 via a phone call as indicated generally at 126. The data, however, is very limited and often does not help with a diagnosis of difficulties with or malfunctions of a medical device 12, resulting in the end-user having to send the device 12 back to its manufacturer for in-depth analysis and troubleshooting. Such a request to return a device to its manufacturer presents many challenges. For example, a user 122 may choose not to send the device 12 back to the manufacturer at all for analysis. If the user 122 elects to return the device 12 to the manufacturer, the user may have to decontaminate device 12. Also, special packaging for shipping the device 12 may be required, which increases costs to the manufacturer. Also, physically shipping a device 12 to its manufacturer for analysis and troubleshooting causes delay in diagnosis of the issue with the device 12 and possible delays in patient treatment while the device is out of service.

In accordance with an illustrative embodiment, a pass-through portal app 128 is provided for a smartphone 16 to permit data on the device 12 to be viewed remotely by customer service personnel 124. Since device 12 data can be sensitive (i.e., requiring privacy protection and/or security against nefarious attacks to device operation, data from the medical device 12 passes through the portal app 128 on the smart device (e.g., smartphone 16) but is not saved on the smart device). The portal app 128 instead relays the medical device 12 data to the cloud 94 via the smartphone 16 and the data resides in the cloud 94 for remote diagnosis. The portal app can be configured, for example, to employ the above-described intradevice Bluetooth® technology (e.g., secure pairing via BLE using 32-bit encryption and no open broadcasts) to exchange data between the portal app 128 and the device 12. Similarly, the cloud 94 can have a cloud-computing device therein that is configured to employ the same intradevice Bluetooth® technology (e.g., secure pairing via BLE using 32-bit encryption and no open broadcasts) to exchange data with the portal app 128. The portal app for securely relaying sensitive device data between the medical device and the cloud 94, and secure access to the data on the cloud 94 by customer service personnel 124, allows customer service personnel 124 to view a snapshot of medical device 12's system data during a customer service call.

As stated above, system data from a medical device 12 is sent to an end-user 122's smart device (e.g., smartphone 16) via a mobile app 128. Once downloaded to the user's device 16, this app 128 can require the user 122 to approve sending device 12 data to the smartphone 16 and then to the manufacturer via the cloud 84 using Wi-Fi or cellular communications as indicated at 130 in FIG. 13. The app 128 is generally a portal that supports a pass-through mode and does not store any data on the smart device 16. The device 12 data is instead stored in the cloud 94 where customer service personnel 124 can view it and troubleshoot the user 122's device 12. Thus, the pass-through app 128 facilitates real-time diagnosing of medical device 12 issues.

For example, an end user 122 calls Customer Service 124 via a toll-free number (step 1). If customer service personnel 124 cannot diagnose or resolve the problem with the device 12 via the initial phone call (step 2) using preliminary data provided by the user 122, the customer service representative 124 gets approval from end user 122 to send medical device 12's data instead of the device 12 itself for more in-depth analysis (step 3). The customer service representative 124 can instruct the user 122 to download the app 128 from the internet (e.g., via Google Play or iPhone App Store) onto the user's smart device 16 (step 4). The customer service representative 124 and/or instructions provided via the app 128 assist the user 122 with completing steps necessary to send device 12 data via the smart device 16 to a secure server 94 that customer service representative can access (step 5). The customer service representative 124 can, in turn, perform in-depth data analysis of the device 12 data (step 6), and can provide the end-user with a solution or at least a diagnosis and/or feedback to end-user 122 in real-time such as before ending the call (step 7).

Figure 14:
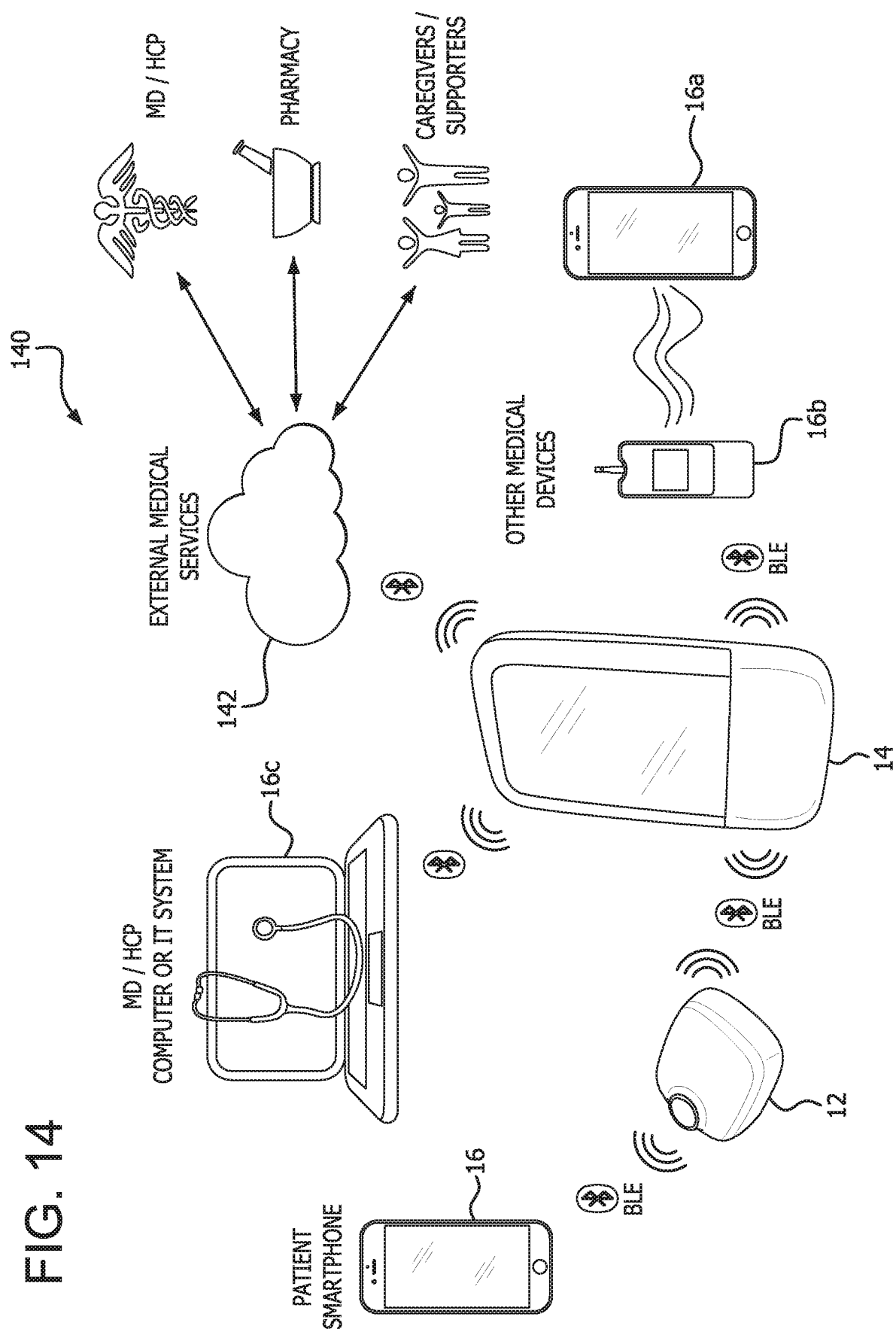
FIG. 14 is an example informatics-enhanced system comprising interconnecting a medical device, medical device controller, and other devices in accordance with an illustrative embodiment.

FIG. 14 illustrates an example embodiment of an IDD 12 and WC 14 with smartphone 16 connected to other devices in an example informatics-enhanced system such as an IDM system 140 that improves consumer health experience through the use of a mobile IDM application and device connectivity. The system 140 provides a highly personalized and relevant content experience to each user where experiences are customized to fit that user's patient journey. For example, actionable insights can be gained from passive tracking of medical/health device data and convenient access to that data. As shown in FIG. 14, the WC 14 can be configured for operation as a hub in a BAN for secure wireless communications (e.g., using intradevice BLE technology) with the IDD 12 and other BAN devices such as a blood glucose (BG) meter 16b and its corresponding smartphone app represented at 16a. The WC 14 can also be configured to use a different interdevice communication protocol (e.g., BLE with broadcast mode) to communicate notifications and historical data from the IDD 12 to the smartphone 16. In addition, the WC 14 can employ the same or yet another interdevice communication protocol to send IDD 12 and BD meter 16b historical data, among other device data, to and receive medical or patient data from a physician/healthcare provider (MD/HCP) computer or computer system indicated at 16c, and/or devices 16d, 16e, . . . , 16n corresponding to MD/HCPs, pharmacy and caregivers who are related to a user in an external medical service system 142. It is to be understood that the IDD 12 can be operated with a smartphone as the WC 14 and therefore also as the hub in accordance with another illustrative embodiment. Advantages of an IDM system 140 are improved customer experiences such as access to best practices, tips and insights on their smartphone 16 IDM app, as well as integrated health and/or disease management coaching services and risk triaging via two-way communication. In addition, the IDM system 140 provides convenient access to consistent and complete clinical data sets (e.g., BG values reported from a connected meter 16b), dosing and titration algorithms, care plan adherence monitoring and integrated emergency medical response (EMR) planning, among other functions).

Figure 15:
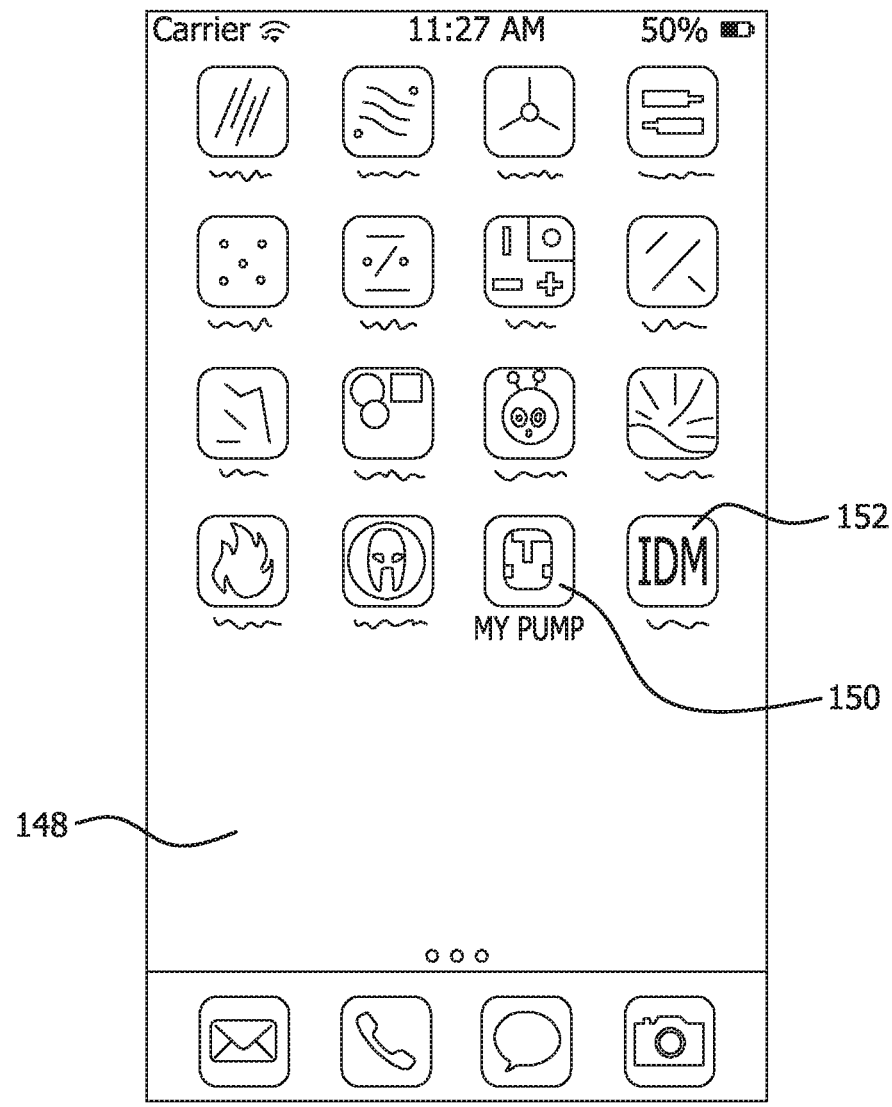

FIG. 15 is an example GUI home screen 148 generated on a smartphone 16 having icons 150 and 152 for opening and accessing, respectively, an IDD 12 control app and an IDM app downloaded and installed to the smartphone 16. Other icons (not shown) can be provided for various medical/health apps such as a BG monitor, an exercise monitoring app, a carbohydrate tracker, an app for capturing data from a drug delivery pen, and so on.

Figure 16:
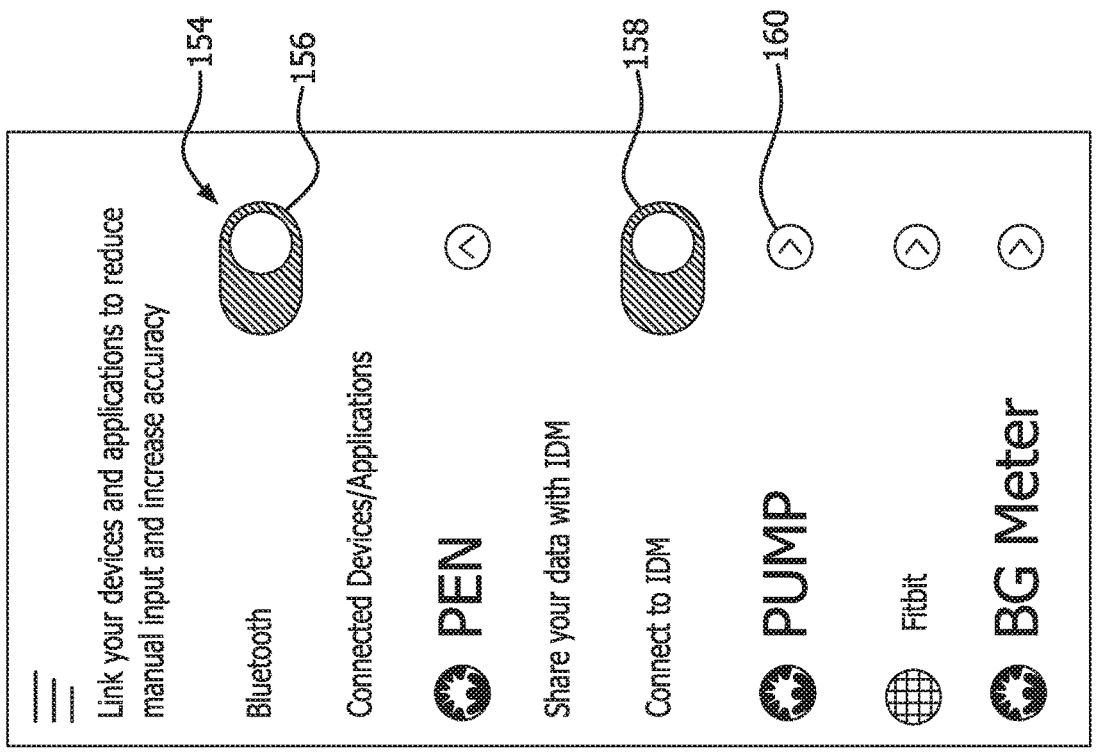
Figure 20:
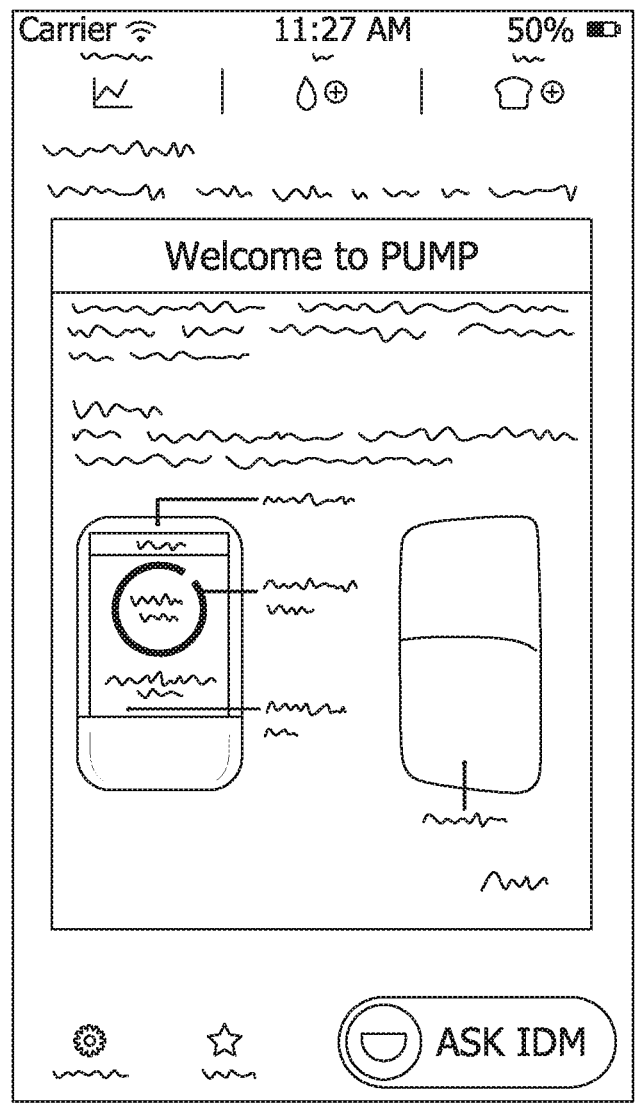
Figure 21:
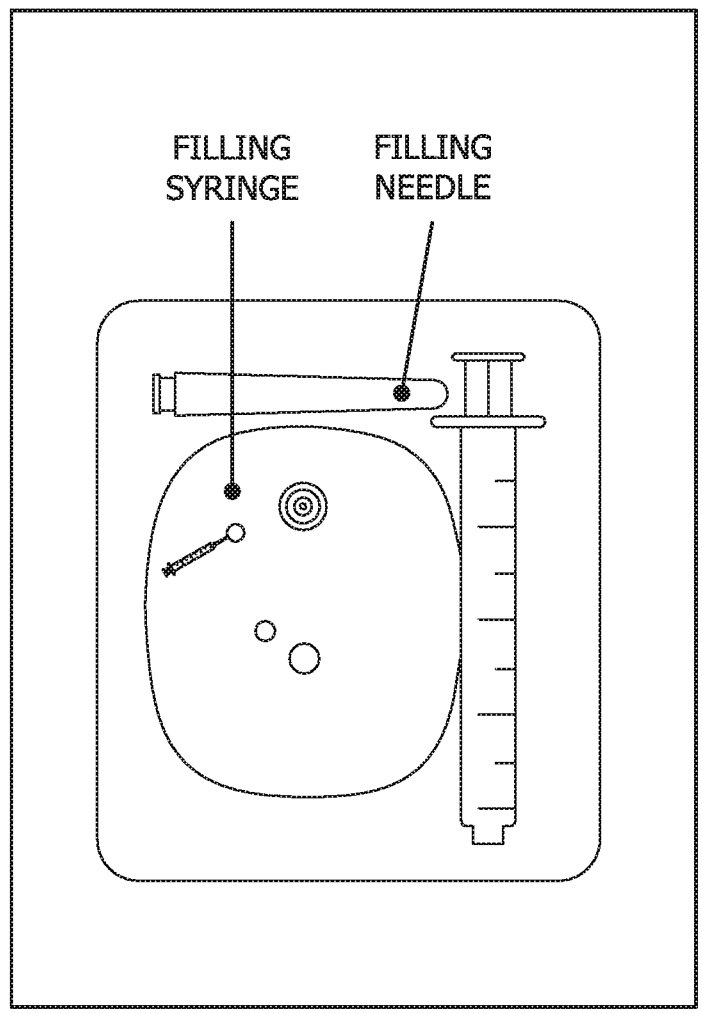
Figure 22:
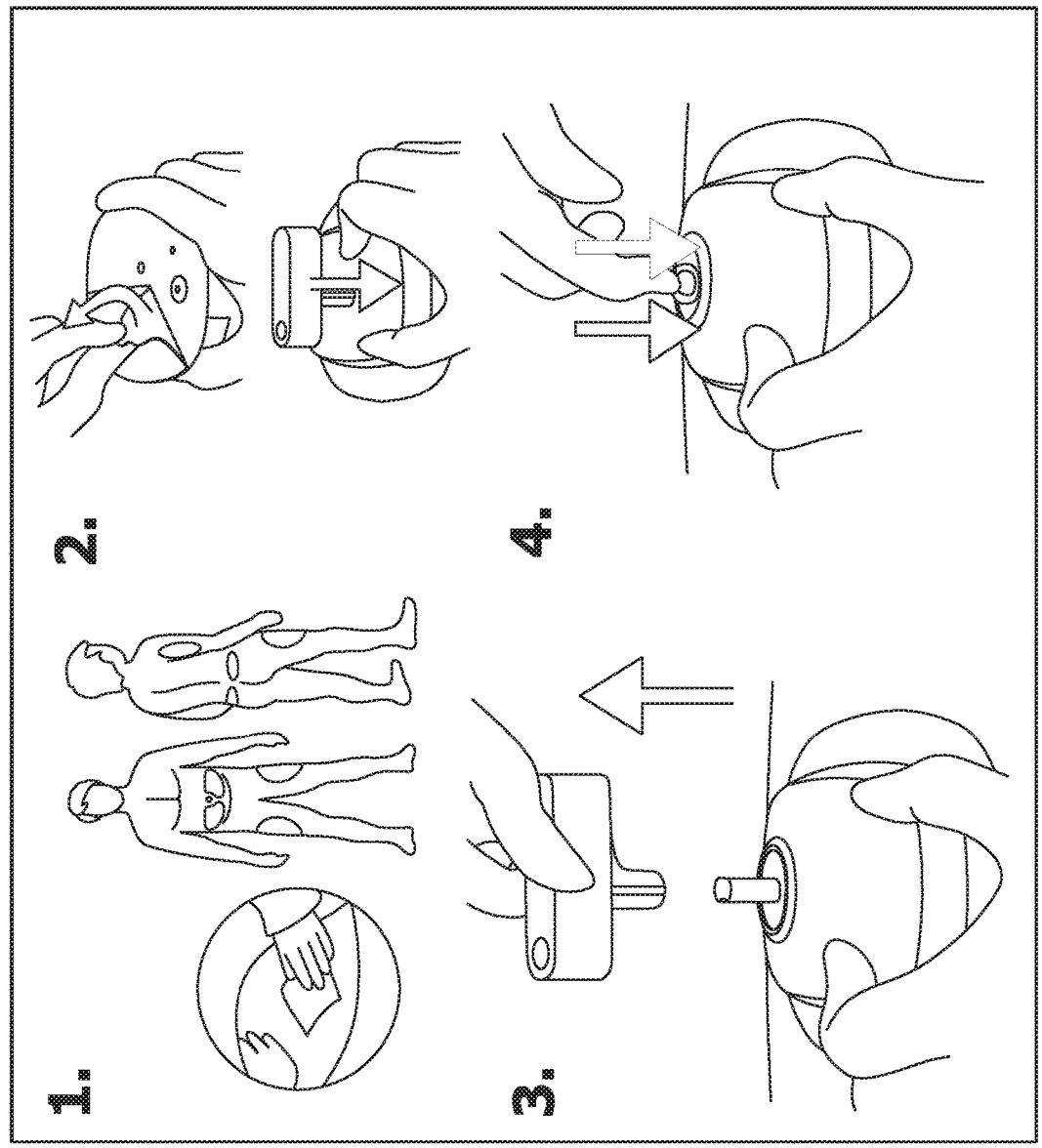
Figure 23:
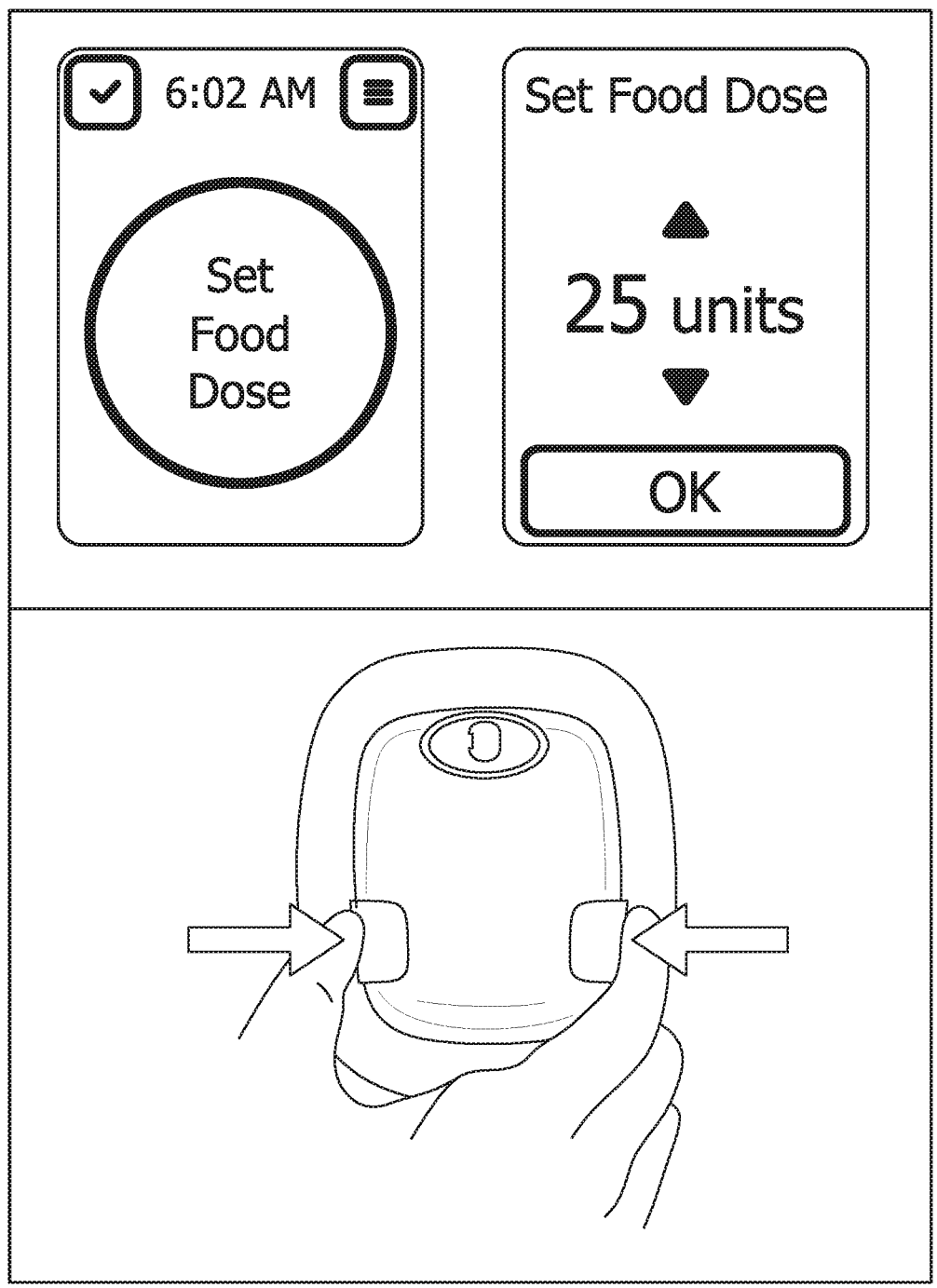

FIG. 16 is an example connected medical/health devices setting screen 154 generated on a smartphone 16 that allows a user to select which medical/health apps on the smartphone 16 can be connected to exchange data via Bluetooth® with other devices 16. For example, a user can turn the smartphone 16's Bluetooth® function on or off using GUI toggle button 156. A list of connected device apps appears on the screen 154 such as a pen app, a pump app (e.g., for the IDD 12), a BG meter app, a Fitbit app, and an IDM app. Each listed app has a select button 158 to expand its view and indicate a toggle button 160 for Bluetooth® connectivity, that is, to allow an app to wirelessly exchange signals with its corresponding connected device, and the IDM app to transfer information to a cloud 94 or other remote IDM computer.

Figure 17:
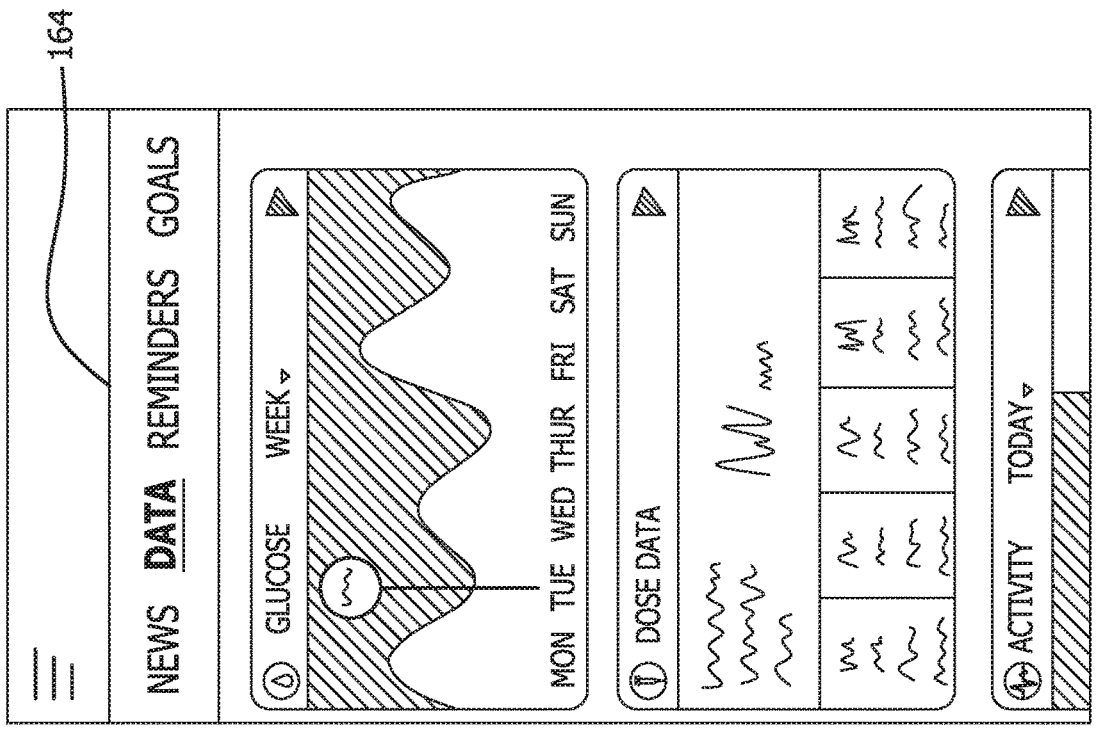

FIG. 17 is an example IDM app home screen 164 generated on a smartphone 16 showing glucose data from a connected BG device, dose data from the IDD 12 and/or connected pen, and activity data (e.g., from a connected Fitbit). FIG. 18 is another example IDM app home screen 166 having buttons 168, 170 and 172 for selecting, respectively, MyData, BG and LOG that can be selected to expand the screen view by listing the corresponding data points (e.g., a history of doses, or BG values, or consumed carbohydrates and/or activity levels) on a separate screen or in a pop-up dialog box. The screen 166 also includes a section 174 providing a message to the user generated using, for example, predictive analysis and machine learning modules and user data such as, but not limited to, any of the following: dates, times and amounts or levels of BG readings and delivered medication, information related to user's level of activity, indication of mood or general well-being, meal data such as ingested carbohydrates, and history of user interactions with the IDM app including chatbot inquiries and responses. The message can be an offer to provide selected information that the user can choose to receive by activating a Tell Me More button 182.

The example IDM app home screen 166 in FIG. 18 also comprises an Ask IDM button 176 that can be selected to cause generation of a screen feature 178 in which alphanumeric text for a user inquiry can be entered as shown in the example chat dialog screen 180 in FIG. 19 that can be generated on the smartphone 16 in response to activation of the button 176.

Example screens in FIGS. 20-23 provide information regarding the IDD 12 in response, for example, to activation of the Tell Me More button 182 (e.g., see screen 166 in FIG. 18) or a corresponding inquiry entered into the screen portion 178 in screen 180 depicted in FIG. 19. FIGS. 20-23 can be respective screens or respective portions of a video playing in a screen that provide the user, for example, an introduction of features of the WC 14, items provided in IDD 12 packaging and how to use them to fill the IDD 12, applying an IDD 12 to a user's skin, and using the IDD 12 to set a bolus or food dose and to manually activate buttons to commence a bolus dose.

In accordance with an illustrative embodiment, security of protected health information (PHI) and personally identifiable information (PI) and other types of personal data and sensitive data is maintained by configuring the IDD 12 and WC 14 to neither transmit nor capture such data. For example, the IDD 12 and the WC 14 are configured to only transmit configuration data (e.g., dosing amounts) between the devices using a secure communication protocol. Further, the IDD 12 and the WC 14 are configured to store configuration data but not PII or PHI. If the IDD 12 and WC communicate with another device(s) 16, the device 16 or its app is configured to also restrict the device to storing configuration or status or log data and no PII or PHI obtained from the connected devices 12, 14 and 16 in the system 10.

In accordance with aspect of an illustrative embodiment, security with respect the IDD 12 and WC 14 can be maintained by not allowing connected devices 16 to monitor the status of IDD or WC. Instead, the WC 14 can be configured to be restricted to transferring only log files to a BWCDI and only after secure pairing with the BWCDI.

In accordance with aspect of an illustrative embodiment, the IDD 12 is configured to receive no maintenance or push updates. For example, the IDD 12 is configured to be disposable and to not require updates during its life cycle. In addition, the WC 14 is also configured to be restricted with regard to service handling. For example, after the initial distribution, the WC is designed to be non-field serviceable (i.e., no parts are permitted to be inspected, adjusted, replaced or maintained by the user), except for replaceable alkaline batteries. As described with reference to the illustrated embodiment in FIG. 13, secure communication of system data from a medical device 12 to a manufacturer, product support team or service customer support personnel can be provided via a pass-through app 128 to provide remote troubleshooting and diagnosis of general system issues and/or to reinforce proper use and maintenance of system to patients and/or caretakers. In addition, the system 10 can employ an internal process to provide end-of-life and end-of-support notifications directly to customers, where appropriate, such as using stored customer data to contact customers via email, voice mail or direct mailing. Alternatively or in addition to the internal process.

The smartphone app(s) 14 and 16 for IDD controller operations and other device communications, respectively, likewise restrict the data captured at, transmitted from and stored in the smartphone 14 or 16 or other connected device 16. In accordance with aspects of illustrative embodiments, the system 10 utilizes a device-specific, Bluetooth®-pairing out-of-band (OOB) association model for pairing the IDD 12 and WC 14 to increase system resistance to a potential MITM attack. Further, no authorization or authentication is required by the WC 14. In other words, anyone with access to the device 14 can utilize and control the device 14, which is advantageous for human factor reasons (e.g., patient and caregiver preferences for ease of use).

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the illustrative embodiments can be easily construed as within the scope of the invention by programmers skilled in the art to which the illustrative embodiments pertain. Method steps associated with the illustrative embodiments can be performed by one or more programmable processors executing a computer program, code or instructions to perform functions (e.g., by operating on input data and/or generating an output). Method steps can also be performed by, and apparatus of the illustrative embodiments can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The above-presented description and figures are intended by way of example only and are not intended to be limiting in any way except as set forth in the following claims. It is particularly noted that persons skilled in the art can readily combine the various technical aspects of the various elements of the various illustrative embodiments that have been described above in numerous other ways.

The invention claimed is:

1. A device for controlling a medical device, comprising:
   a radio frequency (RF) circuit configured to exchange RF signals with the medical device;
   a memory device; and
   a processing device connected to the RF circuit and the memory device and configured to employ a selected one of at least two wireless communication protocols to exchange, via the RF circuit, RF signals with the medical device, wherein the at least two wireless communication protocols comprises a first communication protocol that is employed by the processing device to pair the device with the medical device to securely send secure information chosen from configuration data, medical device operation data, and control signals to operate the medical device, and a second communication protocol that is employed by the processing device to pair with one or more devices different from the medical device and to send information chosen from medical device data and notifications that requires less security than the secure information to the one or more other devices;
   wherein the device is configured to constrain the secure information chosen from the configuration data, the medical device operation data, and the control signals to communication via the first communication protocol by providing the secure information with metadata to signify that the first communication protocol is needed to exchange the secure information between the device and the medical device and to preclude communication of the secured information to the said one or more other devices that do not also employ the first communication protocol.

2. The device of claim 1, wherein the device is selected from the group of a handheld, dedicated controller for the medical device, and a smartphone having a medical device control app stored thereon for execution to control the medical device.

3. The device of claim 1, wherein the first communication protocol limits pairing of the medical device to only the device for controlling operations of the medical device.

4. The device of claim 3, wherein the first communication protocol is a Bluetooth® Low Energy (BLE) communication protocol.

5. The device of claim 4, wherein the BLE communication protocol has no broadcast mode.

6. The device of claim 3, wherein the first communication protocol is specific to the medical device and not usable by the one or more other devices to pair with the device.

7. The device of claim 1, wherein the second communication protocol is a standard Bluetooth® protocol that is employed by the device to pair with the one or more other devices and comprises a broadcast mode to discover the one or more other devices.

8. The device of claim 1, wherein the device is configured to operate as a hub in an integrated disease management (IDM) system by employing the first communication protocol to pair and exchange signals with the medical device, and the second communication protocol to pair and exchange signals with the one or more other devices, wherein the medical device is a medication delivery device and the one or more other devices are selected from the group consisting of a blood glucose monitor, a carbohydrate tracking device, and a physical exercise tracking device.

9. The device of claim 1, further comprising a portal app for passing through data relating to the medical device to another device, the portal app being configured to receive data transmitted from the medical device and provide it to another device and not store the data at the device.

10. The device of claim 1, wherein the processing device is configured to determine which of the first communication protocol and the second communication protocol to employ to transmit signals via the RF circuit depending on a criterion chosen from type of operation requiring transmission of the signals and type of information being sent via the signals.

11. The device of claim 10, wherein the type of operation is chosen from sending a medical device control command, setting a medical device configuration parameter, requesting medical device status data, requesting medical device log data, requesting secure data from the medical device, and transmitting data to the one or more other devices, and the processing device is configured to employ the first communication protocol to perform the type of operation chosen from sending a medical device control command, setting a medical device configuration parameter, and requesting secure data from the medical device, and to employ the second communication protocol to perform the type of operation chosen from requesting medical device status data, requesting medical device log data, and transmitting data to the one or more other devices.

12. The device of claim 1, wherein the one or more other devices are selected from the group consisting of a smart watch, a portable monitoring device, a Bluetooth®-enabled wristband device, a blood glucose monitor, a carbohydrate tracking device, and a physical exercise tracking device.

13. The device of claim 1, further comprising a user interface comprising a graphical user interface (GUI) connected to the processing device, the processing device being configured to display on the GUI at least one screen indicating device application icons corresponding to smartphone applications chosen from a medical device operation application, a blood glucose monitor application, a carbohydrate tracking application, and a physical exercise tracking application, a medication delivery management application, and an integrated disease management application, and at least one application configuration prompt for a user selected setting chosen from Bluetooth® enabled and Bluetooth® disabled for each of the smartphone applications.

14. A medical device, comprising:
   a radio frequency (RF) circuit configured to exchange RF signals with one or more devices different from the medical device;
   a memory device; and
   a processing device connected to the RF circuit and the memory device and configured to employ a selected one of at least two wireless communication protocols to exchange, via the RF circuit, RF signals with the one or more devices, wherein the at least two wireless communication protocols comprises a first communication protocol that is employed by the processing device to pair the medical device with the one or more devices that have been provided with the first communication protocol and medical device identifying information to securely exchange secure information chosen from configuration data, medical device operation data, and control signals to operate the medical device, and a second communication protocol that is employed by the processing device to pair the medical device with the one or more devices to send information chosen from medical device data and notifications that requires less security than the secure information to the one or more devices wherein the medical device is configured to constrain the secure information chosen from the configuration data, the medical device operation data, and the control signals to communication via the first communication protocol when the secure information is determined to comprise metadata that signifies the first communication protocol is needed to exchange the secure information between the device and the medical device and to preclude communication of the secured information to the one or more other devices that do not also employ the first communication protocol; and wherein the medical device is configured to provide the less secure information chosen from the medical device data and the notifications with metadata to signify that the second communication protocol can be used to communicate the less secure information data from the medical device to the one or more devices.

15. The device of claim 14, wherein the one or more devices is selected from the group of a handheld, dedicated controller for the medical device, and a smartphone having a medical device control app stored thereon for execution to control the medical device.

16. The device of claim 14, wherein the first communication protocol limits pairing of the medical device to only a selected one of the one or more devices for controlling operations of the medical device.

17. The device of claim 16, wherein the first communication protocol is a Bluetooth® Low Energy (BLE) communication protocol.

18. The device of claim 17, wherein the BLE communication protocol has no broadcast mode.

19. The device of claim 16, wherein the first communication protocol is specific to the medical device and the selected one of the one or more devices and not usable by remaining ones of the one or more other devices to pair with the medical device.

20. The device of claim 14, wherein the second communication protocol is a standard Bluetooth® protocol that is employed by the medical device to pair with the one or more other devices and comprises a broadcast mode to discover the one or more other devices.

* * * * *